(12) United States Patent
Zhou

(10) Patent No.: US 9,580,515 B2
(45) Date of Patent: Feb. 28, 2017

(54) NEUKINASE, A DOWNSTREAM PROTEIN OF NEUREGULIN

(75) Inventor: Mingdong Zhou, Shanghai (CN)

(73) Assignee: Zensun (Shanghai) Science & Technology, Co., Ltd., Shanghai (CN)

(*) Notice: Subject to any disclaimer, the term of this patent is extended or adjusted under 35 U.S.C. 154(b) by 40 days.

(21) Appl. No.: 11/894,542

(22) Filed: Aug. 20, 2007

(65) Prior Publication Data

US 2008/0260713 A1 Oct. 23, 2008

Related U.S. Application Data

(60) Provisional application No. 60/839,388, filed on Aug. 21, 2006, provisional application No. 60/921,655, filed on Apr. 2, 2007.

(51) Int. Cl.
| | |
|---|---|
| *A61K 38/45* | (2006.01) |
| *C07K 16/40* | (2006.01) |
| *C12N 9/12* | (2006.01) |
| *C12Q 1/48* | (2006.01) |
| *G01N 33/68* | (2006.01) |

(52) U.S. Cl.
CPC ............ *C07K 16/40* (2013.01); *A61K 38/45* (2013.01); *C12N 9/1205* (2013.01); *C12Q 1/485* (2013.01); *G01N 33/68* (2013.01); *G01N 33/6842* (2013.01); *G01N 2333/4756* (2013.01)

(58) Field of Classification Search
CPC ................................ A61K 38/45; C07K 16/40
USPC .............................. 530/387.9, 300; 424/94.5
See application file for complete search history.

(56) References Cited

U.S. PATENT DOCUMENTS

| | | | |
|---|---|---|---|
| 4,736,866 | A | 4/1988 | Leder et al. |
| 4,870,009 | A | 9/1989 | Evans et al. |
| 4,873,191 | A | 10/1989 | Wagner et al. |
| 4,946,778 | A | 8/1990 | Ladner et al. |
| 4,980,286 | A | 12/1990 | Morgan et al. |
| 5,225,539 | A | 7/1993 | Winter |
| 5,272,065 | A | 12/1993 | Inouye et al. |
| 5,530,109 | A | 6/1996 | Goodearl et al. |
| 5,585,089 | A | 12/1996 | Queen et al. |
| 5,716,930 | A | 2/1998 | Goodearl et al. |
| 5,840,697 | A | 11/1998 | Blondelle et al. |
| 5,906,810 | A | 5/1999 | Turner |
| 2007/0083334 | A1* | 4/2007 | Mintz ............... G06F 19/24 702/19 |

FOREIGN PATENT DOCUMENTS

| | | |
|---|---|---|
| WO | WO 90/11354 A1 | 10/1990 |
| WO | WO 91/01140 A1 | 2/1991 |
| WO | WO 93/04169 A1 | 3/1993 |
| WO | WO 97/09425 A1 | 3/1997 |
| WO | 9949062 A1 | 9/1999 |
| WO | WO 00/64400 A2 | 11/2000 |
| WO | WO 02/24889 A2 | 3/2002 |
| WO | WO 02/40683 A2 | 5/2002 |
| WO | WO 03/100046 * | 12/2003 ............... C12N 9/12 |
| WO | WO 2004/050894 A1 | 6/2004 |
| WO | WO 2004/112763 A2 | 12/2004 |
| WO | 2005/018673 A1 | 3/2005 |
| WO | WO 2005/063976 A2 | 7/2005 |
| WO | WO 2005/063983 A1 | 7/2005 |
| WO | WO 2008/128161 A2 | 10/2008 |

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Definition of diluent from http://medical-dictionary.thefreedictionary.com/diluent, pp. 1-3. Accessed Nov. 5, 2014.*
PCT International Search Report dated Nov. 29, 2007, in International Application No. PCT/CN2007/002531, filed Aug. 21, 2007.
Carraway et al., 1997, "Neuregulin-2, a New Ligand of ErbB3/ErbB4-Receptor Tyrosine Kinases," *Nature*, vol. 387:512-516.
Chan et al., 2008, "Identification of Cardiac-Specific Myosin Light Chain Kinase," *Circ. Res.*, vol. 102:571-580.

(Continued)

*Primary Examiner* — Julie Ha
(74) *Attorney, Agent, or Firm* — Jones Day

(57) ABSTRACT

The present invention relates to neukinase, a downstream protein kinase in the neuregulin signaling pathway. In certain aspects, the present invention provides isolated neukinase-encoding nucleic acids, neukinase polypeptides, oligonucleotides that hybridize to neukinase nucleic acids, and expression vectors containing neukinase-encoding sequences. The present invention further provides isolated host cells, antibodies, transgenic non-human animals, compositions, and kits relating to neukinase. In other aspects, the present invention further provides methods of identifying predisposition to cardiac dysfunction, methods of detecting the presence of neukinase, neukinase nucleic acid, methods of screening for agents which affect neukinase activity, and methods of modulating neukinase activity.

13 Claims, 4 Drawing Sheets

(56) References Cited

OTHER PUBLICATIONS

Figure 1:
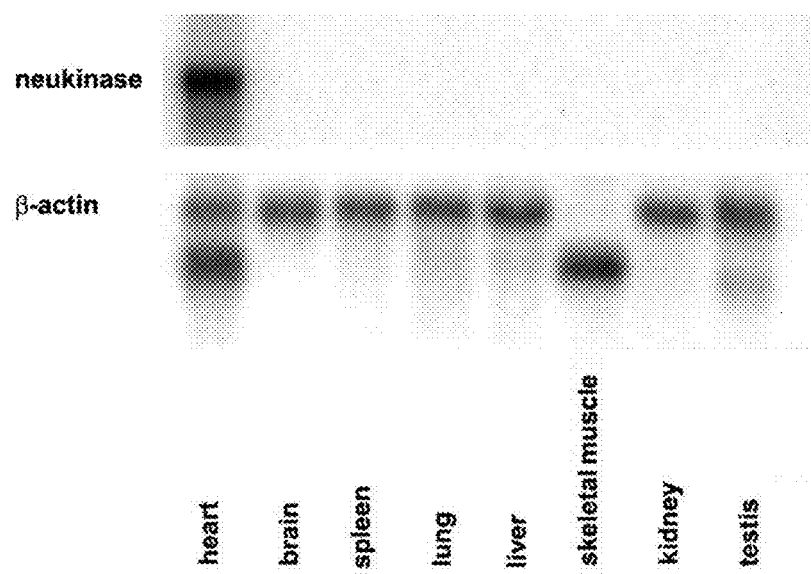

Chang et al., 1997, "Ligands for ErbB-Family Receptors Encoded by a Neuregulin-Like Gene," *Nature*, vol. 387:509-512.
Higashiyama et al., 1997, "A Novel Brain-Derived Member of the Epidermal Growth Factor Family that Interacts with ErbB3 and ErbB4," *J. Biochem*, vol. 122(3):675-680.
Hijazi et al., 1998, "NRG-3 in Human Breast Cancers: Activation of Multiple erb B Family Proteins," *Int. J. Oncol.*, vol. 13:1061-1067.
Holmes et al., 1992, "Identification of Heregulin, a Specific Activator of p185$^{erbB2}$," *Science*, vol. 256:1205-1210.
Macera et al., 1992, "Localization of the Gene Coding for Ventricular Myosin Regulatory Light Chain (MYL2) to Human Chromosome 12q23-q24.3," *Genomics*, vol. 13:829-831; Genbank Accession No. NM00432.
Polak et al., 1991, "A Novel Calmodulin Antagonist, CGS 9343B, Modulates Calcium-Dependent Changes in Neurite Outgrowth and Growth Cone Movements," *J. Neurosci.*, vol. 11(2):534-542.
Seguchi et al., 2007, "A Cardiac Myosin Light Chain Kinase Regulates Sarcomere Assembly in the Vertebrate Heart," *The Journal of Clinical Investigation*, vol. 117(10): 2812-2824.
Siiarma et al., 1979, "Preparation and Assay of the Ca2+-Dependent Mudulator Protein," *Adv. Cyclic Nucleotide Res.*, vol. 10:187-198.
Simpson et al., 1982, "Myocyte Hypertrophy in Neonatal Rat Heart Cultures and its Regulation by Serum and by Catecholamines," *Circulation Res.*, vol. 51:787-801.
Wallace et al., 1983, "Assay of Calmodulin by Ca$^2$ —Dependent Phosphodiesterase," *Methods Enzymol*, vol. 102:39-47.
Genbank Accession No. XM_001064628, Jun. 22, 2006.
Genbank Accession No. AJ247087, Apr. 15, 2005.
EBI Accession No. EMBL:AK146683, Sep. 6, 2005.
EBI Accession No. UniProt:Q3UIZ8, Oct. 11, 2005.
Buchwald et al., "Long-term, continuous intravenous heparin administration by an implantable infusion pump in ambulatory patients with recurrent venous thrombosis," *Surgery*, 88(4):507-516 (1980).
Cohen et al., "Emerging technologies for sequencing antisense oligonucleotides: capillary electrophoresis and mass spectrometry," *Adv. Chromatogr.*, 36:127-162 (1996).
Cole et al., *Monoclonal Antibodies and Cancer Therapy*,Alan R. Liss, Inc., pp. 77-96 (1985).
Cote et al., "Generation of human monoclonal antibodies reactive with cellular antigens," *Proc. Natl. Acad. Sci., U.S.A.*, 80(7):2026-2030 (1983).
Cronin et al., "Cystic fibrosis mutation detection by hybridization to light-generated DNA probe arrays," *Hum. Mutat.*, 7(3):244-255 (1996).
During et al., "Controlled release of dopamine from a polymeric brain implant: in vivo characterizaiton," *Ann. Neurol.*, 25(4):351-356 (1989).
Goodson, in *Medical Applications of Controlled Release*, vol. 2, pp. 115-138 (1984).
Griffin et al., "DNA sequencing. Recent innovations and future trends," *Appl. Biochem. Biotechnol.*, 38(1-2):147-159 (1993).
Howard et al., "Intracerebal drug delivery in rats with lesion-induced memory deficits," *J. Neurosurg.*, 71(1):105-112 (1989).
Huse et al., "Generation of a large combinatorial library of the immunoglobulin repertoire in phage lambda," *Science*, 246(4935):1275-1281 (1989).
Joliot et al., "Antennapedia homebox peptide regulates neural morphogenesis," *Proc. Natl. Acad. Sci., U.S.A.*, 88(5):1864-1868 (1991).
Köhler et al., "Continuous cultures of fused cells antibody of predifined specificity," *Nature*, 256(5517):495-497 (1975).
Kozal et al., "Extensive polymorphisms observed in HIV-1 clade B protease gene using high-density oligonucleotide arrays," *Nat. Med.*, 2(7):753-759 (1996).
Kozbor et al., "The production of monoclonal antibodies from human lymphocytes," *Immunol. Today*, 4(3):72-79 (1983).
Lakso et al., "Targeted oncogene activation by site-specific recombination in transgenic mice," *Proc. Natl. Acad. Sci., U.S.A.*, 89(14):6232-6236 (1992).
Langer et al., "Chemical and physical structure of polymers as carriers for controlled release of bioactive agents: a review," *J. Macromol. Sci. Rev. Macromol. Chem. Phys.*, 23(1):61-126 (1983).
Langer, "New methods of drug delivery," *Science*, 249(4976):1527-1533 (1990).
Levy et al , "Inhibition of calcification of bioprosthetic heart valves by local controlled-release disphosphonate," *Science*, 228(4696):190-192 (1985).
Li et al., "Targeted mutation of the DNA methyltransferase gene results in embryonic lethality," *Cell*, 69(6):915-926 (1992).
Lopez-Berestein, "Treatment of systemic fungal infections with liposomal-amphotericin B," *Liposomes in the Therapy of Infectious Disease and Cancer*, Lopez-Berestein and Fidler (eds.), Liss, New York, pp. 317-372 (1989).
Maxam et al., "A new method for sequencing DNA," *Proc. Natl. Acad. Sci., U.S.A.*, 74(2):560-564 (1977).
Morrison et al., "Chimeric human antibody molecules: mouse antigen-binding domains with human constant region domains," *Proc. Natl. Acad. Sci., U.S.A.*, 81(21):6851-6855 (1984).
Naeve et al., "Accuracy of automated DNA sequencing: a multi-laboratory comparison of sequencing results," *Biotechniques*, 19(3):448-453 (1995).
Neuberger et al., "Recombinant antibodies possessing novel effector funtions," *Nature*, 312(5995):604-608 (1984).
O'Gorman et al., "Recombinase-mediated gene activation and site-specific integration in mammalian cells," *Science*, 251(4999):1351-1355 (1991).
Saiki et al., "Analysis of enzymatically amplified beta-globin and HLA-DQα DNA with allele-specific oligonucleotide probes," *Nature*, 324(6093):163-166 (1986).
Saiki et al., "Genetic analysis of amplified DNA with immobilized sequence-specific oligonucleotide probes," *Proc. Natl. Acad. Sci. U.S.A.*, 86(16):6230-6234 (1989).
Sanger et al., "DNA sequencing with chain-terminating inhibitors," *Proc. Natl. Acad. Sci., U.S.A.*, 74(12):5463-5467 (1977).
Saudek et al., "A preliminary trial of the programmable implantable medication system for insulin delivery," *N. Engl. J. Med.*, 321(9):574-579 (1989).
Sefton, "Implantable pumps," *Crit. Rev. Biomed. Eng.*, 14(3):201-240 (1987).
Takeda et al., "Construction of chimaeric processed immunoglobulin genes containing mouse variable and human constant region sequences," *Nature*, 314(6010):452-454 (1985).
The Fantom Consrtium et al., "The transcriptional landscape of the mammalian genome," *Science*, 309:1559-1563 (2005).
Thomas et al., "Site-directed mutagenesis by gene targeting in mouse embryo-derived stem cells," *Cell*, 51(3):503-512 (1987).
Treat et al., "Liposome encapsulated doxorubicin preliminary results of phase I and phase II trials," *Liposomes in the Therapy of Infectious Disease and Cancer*, Lopez-Berestein and Fidler (eds.), Liss, New York, pp. 353-365 (1989).
Wilmut et al., "Viable offspring derived from fetal and adult mammalian cells," *Nature*, 385(6619):810-813 (1997).
Wu et al., "Receptor-mediated in vitro gene transformation by a soluble DNA carrier system," *J. Biol. Chem.*, 262(10):4429-4432 (1987).

\* cited by examiner

FIGURE 4

SEQUENCE LISTING

```
<160> NUMBER OF SEQ ID NOS: 26

<210> SEQ ID NO 1
<211> LENGTH: 786
<212> TYPE: PRT
<213> ORGANISM: Rattus

<400> SEQUENCE: 1

Met Ser Gly Val Ser Glu Glu Asp Pro Glu Gly Leu Gly Pro Gln Gly
1               5                   10                  15
```

-continued

```
Leu Pro Ala Leu Gly Gly Ala Cys Leu Val Thr Val Asp Lys Lys Leu
             20                  25                  30
Asn Val Leu Thr Glu Lys Val Asp Arg Leu Leu His Phe Gln Glu Asp
         35                  40                  45
Val Thr Glu Lys Leu Gln Cys Val Cys Gln Gly Met Asp His Leu Glu
     50                  55                  60
Gln Gly Leu His Arg Leu Glu Ala Ser Gln Glu Leu Gly Leu Ala Gly
 65                  70                  75                  80
Pro Gly Ser Thr Ser Pro Ala Ala Ala Gln Ala Ala Trp Pro Glu Val
                 85                  90                  95
Leu Glu Leu Val Arg Ala Val Arg Gln Glu Gly Ala Gln His Gly Ala
            100                 105                 110
Arg Leu Glu Ala Leu Phe Lys Met Val Val Ala Val Asp Arg Ala Ile
        115                 120                 125
Thr Leu Val Gly Ser Thr Ile Gln Asn Ser Lys Val Asp Asp Phe Ile
130                 135                 140
Leu Gln Gly Thr Val Pro Trp Arg Lys Gly Ser Leu Ala Asp Gly Pro
145                 150                 155                 160
Glu Glu Asn Lys Glu Gln Ala Glu Val Ala Gly Val Lys Pro Lys His
                165                 170                 175
Val Leu Asn Thr Gly Ser Val Gln Ala Ala Thr Ser Arg Ala Leu Trp
            180                 185                 190
Glu Glu Ser Gln Lys Gln Asp Thr Pro Val Gly Thr Val Glu Gly Leu
        195                 200                 205
Pro Leu Ile Ile Asp Thr Ser Leu Lys Gly Ala Asp Leu Thr Gln Ala
210                 215                 220
Gly Ala Ser Leu Arg Gln Gly Val Glu Ala Leu Asp Pro Gly Gln Glu
225                 230                 235                 240
Pro Pro Pro Thr Glu Ala Glu Ser Arg Leu Pro Ala Leu Ala Ser Glu
                245                 250                 255
Asp Thr Gly Thr Thr Leu Glu Leu Ser Val Ala Ile Asp Arg Ile Ser
            260                 265                 270
Glu Val Leu Thr Ser Leu Arg Met Ser Gln Ser Ala Gly Glu Gly Thr
        275                 280                 285
Ser Ser Ser Lys Pro Asp Cys Ser Glu Pro Gly Pro Gln Pro Leu Gly
290                 295                 300
Pro Leu Thr Thr Asp Ser Asp Ile His Ser Asp Glu Gly Leu Pro Arg
305                 310                 315                 320
Ile Ser Val Arg Met Arg Glu Met Thr Thr Pro Glu Glu Leu Phe Glu
                325                 330                 335
Thr Gln Gly Gly Ser Pro Ile Gly Ser Ala Glu Ala Pro Gly Pro Gly
            340                 345                 350
Thr Val Leu Glu Asp Gln Ile Pro Lys Gly Ala Arg Pro Phe Pro Pro
        355                 360                 365
Leu Pro Lys Arg Ser Cys Asn Asn Gly Gly Ala Ser Ala Glu Glu Ala
370                 375                 380
Thr Gly Pro Gly Ala Glu Pro Ile Arg Gly Pro Ser Leu Val Thr Arg
385                 390                 395                 400
Asp Trp Arg Asp Glu Pro Val Gly Thr Thr Asp Leu Gln Gln Gly Arg
                405                 410                 415
Asp Pro Gly Ala Val Ser Pro Glu Pro Gly Lys Asp His Ala Ala Gln
            420                 425                 430
Gly Pro Gly Arg Thr Glu Ala Gly Arg Arg Val Ser Ser Ala Ala Glu
```

```
                435               440              445
Ala Ala Ile Val Val Leu Gly Asp Ser Ala Ala Pro Pro Ala Pro Phe
    450                   455                460
Glu His Arg Val Val Ser Ile Lys Asp Thr Leu Ile Ser Thr Ser Tyr
465                   470                  475                480
Thr Val Ser Gln His Glu Val Leu Gly Gly Arg Phe Gly Gln Val
                485                  490                  495
His Arg Cys Thr Glu Arg Ser Thr Gly Leu Ala Leu Ala Ala Lys Ile
            500                  505                510
Ile Lys Val Lys Asn Ile Lys Asp Arg Glu Asp Val Lys Asn Glu Ile
        515                  520                  525
Asn Ile Met Asn Gln Leu Ser His Val Asn Leu Ile Gln Leu Tyr Asp
    530                  535                  540
Ala Phe Glu Ser Lys Asn Ser Phe Thr Leu Ile Met Glu Tyr Val Asp
545                  550                  555                560
Gly Gly Glu Leu Phe Asp Arg Ile Thr Asp Glu Lys Tyr His Leu Thr
                565                  570                  575
Glu Leu Asp Val Val Leu Phe Thr Arg Gln Ile Cys Glu Gly Val His
            580                  585                  590
Tyr Leu His Gln His Tyr Ile Leu His Leu Asp Leu Lys Pro Glu Asn
        595                  600                  605
Ile Leu Cys Val Ser Gln Thr Gly His Gln Ile Lys Ile Ile Asp Phe
    610                  615                  620
Gly Leu Ala Arg Arg Tyr Lys Pro Arg Glu Lys Leu Lys Val Asn Phe
625                  630                  635                640
Gly Thr Pro Glu Phe Leu Ala Pro Glu Val Val Asn Tyr Glu Phe Val
                645                  650                  655
Ser Phe Pro Thr Asp Met Trp Ser Val Gly Val Ile Thr Tyr Met Leu
            660                  665                  670
Leu Ser Gly Leu Ser Pro Phe Leu Gly Glu Thr Asp Ala Glu Thr Met
        675                  680                  685
Asn Phe Ile Val Asn Cys Ser Trp Asp Phe Asp Ala Asp Thr Phe Lys
    690                  695                  700
Gly Leu Ser Glu Glu Ala Lys Asp Phe Val Ser Arg Leu Leu Val Lys
705                  710                  715                720
Glu Lys Ser Cys Arg Met Ser Ala Thr Gln Cys Leu Lys His Glu Trp
                725                  730                  735
Leu Asn His Leu Ile Ala Lys Ala Ser Gly Ser Asn Val Arg Leu Arg
            740                  745                  750
Ser Gln Leu Leu Leu Gln Lys Tyr Met Ala Gln Arg Lys Trp Lys Lys
        755                  760                  765
His Phe His Val Val Thr Ala Val Asn Arg Leu Arg Lys Phe Pro Thr
    770                  775                  780
Cys Pro
785

<210> SEQ ID NO 2
<211> LENGTH: 795
<212> TYPE: PRT
<213> ORGANISM: Homo sapiens

<400> SEQUENCE: 2

Met Asp Thr Lys Leu Asn Met Leu Asn Glu Lys Val Asp Gln Leu Leu
1               5                   10                  15
```

-continued

```
His Phe Gln Glu Asp Val Thr Glu Lys Leu Gln Ser Met Cys Arg Asp
             20                  25                  30

Met Gly His Leu Glu Arg Gly Leu His Arg Leu Glu Ala Ser Arg Ala
         35                  40                  45

Pro Gly Pro Gly Gly Ala Asp Gly Val Pro His Ile Asp Thr Gln Ala
     50                  55                  60

Gly Trp Pro Glu Val Leu Glu Leu Val Arg Ala Met Gln Gln Asp Ala
 65                  70                  75                  80

Ala Gln His Gly Ala Arg Leu Glu Ala Leu Phe Arg Met Val Ala Ala
                 85                  90                  95

Val Asp Arg Ala Ile Ala Leu Val Gly Ala Thr Phe Gln Lys Ser Lys
             100                 105                 110

Val Ala Asp Phe Leu Met Gln Gly Arg Val Pro Trp Arg Arg Gly Ser
         115                 120                 125

Pro Gly Asp Ser Pro Glu Glu Asn Lys Glu Arg Val Glu Glu Glu Gly
     130                 135                 140

Gly Lys Pro Lys His Val Leu Ser Thr Ser Gly Leu Gln Ser Asp Ala
145                 150                 155                 160

Arg Glu Pro Gly Glu Glu Ser Gln Lys Ala Asp Val Leu Glu Arg Thr
                 165                 170                 175

Ala Glu Arg Leu Pro Pro Ile Arg Ala Ser Gly Leu Gly Ala Asp Pro
             180                 185                 190

Ala Gln Ala Val Val Ser Pro Gly Gln Gly Asp Gly Val Pro Gly Pro
         195                 200                 205

Ala Gln Ala Phe Pro Gly His Leu Pro Leu Pro Thr Lys Val Glu Ala
     210                 215                 220

Lys Ala Pro Glu Thr Pro Ser Glu Asn Leu Arg Thr Gly Leu Glu Leu
225                 230                 235                 240

Ala Pro Ala Pro Gly Arg Val Asn Val Val Ser Pro Ser Leu Glu Val
                 245                 250                 255

Ala Pro Gly Ala Gly Gln Gly Ala Ser Ser Ser Arg Pro Asp Pro Glu
             260                 265                 270

Pro Leu Glu Glu Gly Thr Arg Leu Thr Pro Gly Pro Gly Pro Gln Cys
         275                 280                 285

Pro Gly Pro Pro Gly Leu Pro Ala Gln Ala Arg Ala Thr His Ser Gly
     290                 295                 300

Gly Glu Thr Pro Pro Arg Ile Ser Ile His Ile Gln Glu Met Asp Thr
305                 310                 315                 320

Pro Gly Glu Met Leu Met Thr Gly Arg Gly Ser Leu Gly Pro Thr Leu
                 325                 330                 335

Thr Thr Glu Ala Pro Ala Ala Gln Pro Gly Lys Gln Gly Pro Pro
             340                 345                 350

Gly Thr Gly Arg Cys Leu Gln Ala Pro Gly Thr Glu Pro Gly Glu Gln
         355                 360                 365

Thr Pro Glu Gly Ala Arg Glu Leu Ser Pro Leu Gln Glu Ser Ser Ser
     370                 375                 380

Pro Gly Gly Val Lys Ala Glu Glu Gln Arg Ala Gly Ala Glu Pro
385                 390                 395                 400

Gly Thr Arg Pro Ser Leu Ala Arg Ser Asp Asp Asn Asp His Glu Val
                 405                 410                 415

Gly Ala Leu Gly Leu Gln Gln Gly Lys Ser Pro Gly Ala Gly Asn Pro
             420                 425                 430

Glu Pro Glu Gln Asp Cys Ala Ala Arg Ala Pro Val Arg Ala Glu Ala
```

```
            435                 440                 445
Val Arg Arg Met Pro Gly Ala Glu Ala Gly Ser Val Val Leu Asp
450                 455                 460

Asp Ser Pro Ala Pro Ala Pro Phe Glu His Arg Val Val Ser Val
465                 470                 475                 480

Lys Glu Thr Ser Ile Ser Ala Gly Tyr Glu Val Cys Gln His Glu Val
                485                 490                 495

Leu Gly Gly Gly Arg Phe Gly Gln Val His Arg Cys Thr Glu Lys Ser
                500                 505                 510

Thr Gly Leu Pro Leu Ala Ala Lys Ile Ile Lys Val Lys Ser Ala Lys
                515                 520                 525

Asp Arg Glu Asp Val Lys Asn Glu Ile Asn Ile Met Asn Gln Leu Ser
                530                 535                 540

His Val Asn Leu Ile Gln Leu Tyr Asp Ala Phe Glu Ser Lys His Ser
545                 550                 555                 560

Cys Thr Leu Val Met Glu Tyr Val Asp Gly Gly Glu Leu Phe Asp Arg
                565                 570                 575

Ile Thr Asp Glu Lys Tyr His Leu Thr Glu Leu Asp Val Val Leu Phe
                580                 585                 590

Thr Arg Gln Ile Cys Glu Gly Val His Tyr Leu His Gln His Tyr Ile
                595                 600                 605

Leu His Leu Asp Leu Lys Pro Glu Asn Ile Leu Cys Val Asn Gln Thr
610                 615                 620

Gly His Gln Ile Lys Ile Ile Asp Phe Gly Leu Ala Arg Arg Tyr Lys
625                 630                 635                 640

Pro Arg Glu Lys Leu Lys Val Asn Phe Gly Thr Pro Glu Phe Leu Ala
                645                 650                 655

Pro Glu Val Val Asn Tyr Glu Phe Val Ser Phe Pro Thr Asp Met Trp
                660                 665                 670

Ser Val Gly Val Ile Thr Tyr Met Leu Leu Ser Gly Leu Ser Pro Phe
                675                 680                 685

Leu Gly Glu Thr Asp Ala Glu Thr Met Asn Phe Ile Val Asn Cys Ser
690                 695                 700

Trp Asp Phe Asp Ala Asp Thr Phe Glu Gly Leu Ser Glu Glu Ala Lys
705                 710                 715                 720

Asp Phe Val Ser Arg Leu Leu Val Lys Glu Lys Ser Cys Arg Met Ser
                725                 730                 735

Ala Thr Gln Cys Leu Lys His Glu Trp Leu Asn Asn Leu Pro Ala Lys
                740                 745                 750

Ala Ser Arg Ser Lys Thr Arg Leu Lys Ser Gln Leu Leu Leu Gln Lys
                755                 760                 765

Tyr Ile Ala Gln Arg Lys Trp Lys Lys His Phe Tyr Val Val Thr Ala
                770                 775                 780

Ala Asn Arg Leu Arg Lys Phe Pro Thr Ser Pro
785                 790                 795

<210> SEQ ID NO 3
<211> LENGTH: 2728
<212> TYPE: DNA
<213> ORGANISM: Rattus

<400> SEQUENCE: 3
caagggcctg ggccaaactc agcctgtcgc tctctcagtg gttgagtggg agatagacac    60
agagaacttg gccctctccg tcccccacac agttcagtca ggaggacagg ttggttccct   120
```

```
gcagcaaggc tcttagcagc ggaggacaat ggccttccag acgttaccac caaagtgaga    180
agcagaccct tcgtgctcca gtttccttgt ctttgccctt accaaaccag aattgggatg    240
tcaggagttt cagaggagga tccagagggt ctgggcccc agggtctgcc agcgttgggc    300
ggagcctgct tagtcaccgt ggacaaaaaa cttaatgtgc tgactgagaa ggtcgacaga    360
ctcttgcatt ccaagaaga tgtcacagag aagctacagt gtgtgtgcca aggcatggat    420
cacctggaac aaggtctgca tcggctggag gcctcccagg agttgggtct ggcagggccc    480
ggcagcactt ccccagccgc tgctcaggcc gcatggcctg aggtcctgga gctggtgagg    540
gccgtgcggc aggagggtgc ccagcacggt gccaggctcg aagccctctt caagatggtg    600
gtggctgtgg acagggctat tactttggta gggtccacaa tccagaactc caaagtggat    660
gatttcatcc tgcaagggac cgtgccctgg aggaaaggca gtctggctga tggccctgag    720
gagaacaagg agcaagcaga agtggctgga gtgaagccaa gcatgtgct gaatacagga    780 agtgtgcaag ctgccacttc tagggcgctg tgggaagaga ccagaagca ggacacaccc    840 gtggggacag tggagggct gcctctcatc atcgatacgt cactgaaggg agctgacctc    900
acccaggctg gagcctcact gaggcaggga gttgaagctc ttgacccagg ccaagaaccc    960
ccacccacag aggcagaatc caggcttcct gcactagcca gcgaggacac tgggaccacc   1020
ctggaattgt ctgtagcaat tgacagaatc agtgaggtcc tcactagcct caggatgtcc   1080
caaagtgctg gcgaaggaac ctcatccagc aagcctgact gttcagagcc tggccctcag   1140
cccctagggc cactaactac agacagtgac attcacagtg atgaaggact tcccaggatc   1200
tctgtccgta tgcgagagat gactactcct gaggagctgt ttgagaccca aggtggcagc   1260
cccattggct cggcagaagc tccaggcct ggaactgtgt tagaagacca gatccctaaa   1320
ggagccagac catttccacc cctgccaaag aggagctgca acaatggtgg cgcgagtgca   1380
gaggaggcaa cagggcctgg ggctgagccc atcagaggac caagcttggt cacaagggac   1440
tggagagatg aacctgttgg gaccacagac ctgcagcaag gcagagaccc aggagcggtg   1500
agccctgaac ctgggaagga ccatgcagcc cagggcccag ggagaaccga agctggaagg   1560
agggtgtctt ctgctgcaga ggctgccatc gtagttctag gtgacagcgc agcaccccca   1620
gccccttttg aacaccgggt agtgagcatc aaagacaccc tcatctcgac aagttacaca   1680
gtgtcccaac acgaagtctt gggaggggc cggtttggcc aggtgcacag gtgtacagag   1740
cggtccacag gccttgcact ggcagccaag atcatcaaag tgaagaacat aaaggaccgg   1800
gaggatgtga agaatgagat caacatcatg aaccagctca gccacgtaaa cttgatccaa   1860
ctttatgatg ctttgagag caagaacagc ttcaccctga tcatggagta tgtggatgga   1920
ggtgaactct tcgaccggat cacgatgag aagtaccacc tgaccgagct ggatgtggtc   1980
ttgttcacaa ggcagatctg tgagggtgtg cattacctgc accagcacta cattctgcac   2040
ctggacctca gccagagaa catactgtgt gtcagccaga ctgggcatca aattaagatt   2100
attgactttg ggctggctag aagatataaa cctcgggaga agctaaaggt taactttggt   2160
actccagagt tcctggctcc agaagttgtt aactatgagt ttgtctcatt cccaacagac   2220
atgtggagtg tgggagttat cacctacatg ctactcagtg gtttgtcccc atttctaggg   2280
gaaacagatg cagagaccat gaattttatt gtgaactgca gctgggattt cgatgctgat   2340
accttcaaag ggctgtcaga ggaagccaag gactttgttt cacggttgct ggtcaaagag   2400
aagagttgta ggatgagcgc cacacagtgc ctgaaacatg agtggttaaa tcacctgatt   2460
```

-continued

| | |
|---|---|
| gccaaagcct caggctccaa cgttcgcctc agatcccaac tactgctgca gaaatatatg | 2520 |
| gctcagcgta aatggaagaa acatttccat gtggtgactg cagtcaacag gctaagaaaa | 2580 |
| tttccaacgt gtccctaatc tacaactggg cctgggagtt cctgaggcga cacgcagtgg | 2640 |
| taatgtgaag agatgactca ggattttatg gagtcaggag cttggctgtt attgatctta | 2700 |
| ttttgcaaag aatggtggaa ggaagaaa | 2728 |

<210> SEQ ID NO 4
<211> LENGTH: 2648
<212> TYPE: DNA
<213> ORGANISM: Homo sapiens

<400> SEQUENCE: 4

| | |
|---|---|
| ctatagggcg acatatgatc gatgatatcc catgggcggc cgcctgcaga ccaggtctga | 60 |
| caccaccgcc tgagtgagaa ccaggggtct gtgcctctcc tcattccccg ctcttgccct | 120 |
| tgtcaagcct gcaccagcat gtcaggaacc tccaaggaga gtctggggca tgggggggctg | 180 |
| ccagggttgg gcaagacctg cttaacaacc atggacacaa agctgaacat gctgaacgag | 240 |
| aaggtggacc agctcctgca cttccaagaa gatgtcacag agaagttgca gagcatgtgc | 300 |
| cgagacatgg gccacctgga gcggggcctg cacaggctgg aggcctcccg ggcaccgggc | 360 |
| ccgggcgggg ctgatggggt tccccacatt gacacccagg ctgggtggcc cgaggtcctg | 420 |
| gagctggtga gggccatgca gcaggatgcg gcccagcacg tgccaggct ggaggccctc | 480 |
| ttcaggatgg tggctgcggt ggacagggcc atcgctttgg tggggccac gttccagaaa | 540 |
| tcaaaggtgg cggatttcct catgcagggg cgtgtgccct ggaggagagg cagcccaggt | 600 |
| gacagccctg aggagaataa agagcgagtg gaagaagagg gaggaaaacc aaagcatgtg | 660 |
| ctgagcacca gtggggtgca gtctgatgcc agggagcctg gggaagagag ccagaaggcg | 720 |
| gacgtgctgg aggggacagc ggagaggctg ccccccatca gagcgtcagg gctgggagct | 780 |
| gaccccgccc aggcagtggt ctcaccgggc caggagatg tgttcctgg cccagcccag | 840 |
| gcattccctg gccacctgcc cctgcccaca aaggtggaag ccaaggctcc tgagacaccc | 900 |
| agcgagaacc tcaggactgg cctggaattg gctccagcac ccggcagggt caatgtggtc | 960 |
| tccccgagcc tggaggttgc accaggtgca ggacaaggag catcgtccag caggcctgac | 1020 |
| cctgagccct tagaggaagg cacgaggctg actccagggc ctggccctca gtgcccaggg | 1080 |
| cctccagggc tgccagccca ggccagggca acccacagtg gtggagaaac acctccaagg | 1140 |
| atctccatcc acatacaaga gatggatact cctggggaga tgctgatgac aggcaggggc | 1200 |
| agccttggac ccaccctcac cacagaggct ccagcagctg cccagccagg caagcagggc | 1260 |
| ccacctggga ccgggcgctg cctccaagcc cctgggactg agcccggaga acagacccct | 1320 |
| gaaggagcca gagagctctc cccgctgcag gagagcagca gccccggggg agtgaaggca | 1380 |
| gaggaggagc aaagggctgg ggccgagcct ggcacgagac caagcttggc caggagtgac | 1440 |
| gacaatgacc acgaggttgg ggccctgggc ctgcagcagg gcaaaagccc aggggcggga | 1500 |
| aaccctgagc ctgagcagga ctgtgcagcc agggctccgg tgagagctga agcagtaagg | 1560 |
| aggatgcccc caggcgccga ggctggcagc gtggttctgg atgacagtcc ggccccacca | 1620 |
| gctcctttg aacaccgggt agtgagcgtc aaggagacct ccatctctgc gggttacgag | 1680 |
| gtgtgccagc acgaagtctt ggagggggt cggtttggcc aggtccacag gtgcacagag | 1740 |
| aagtccacag gcctcccact ggctgccaag atcatcaaag tgaagagcgc caaggaccgg | 1800 |
| gaggacgtga agaacgagat caacatcatg aaccagctca gccacgtgaa cctgatccag | 1860 |

```
ctctatgacg ccttcgagag caagcacagc tgcacccttg tcatggagta cgtggacggg    1920
ggtgagctct tcgaccggat cacagatgag aagtaccacc tgactgagct ggatgtggtc    1980
ctgttcacca ggcagatctg tgagggtgtg cattacctgc accagcacta catcctgcac    2040
ctggacctca agccgagaaa catattgtgc gtcaatcaga caggacatca aattaagatc    2100
attgactttg ggctggccag aaggtacaag cctcgagaga agctgaaggt gaacttcggc    2160
actcctgagt tcctggcccc agaagtcgtc aattatgagt ttgtctcatt ccccacagac    2220
atgtggagtg tgggagtcat cacctacatg ctactcagtg gcttgtcccc atttctaggg    2280
gaaacagatg cagagaccat gaatttcatt gtaaactgta gctgggattt tgatgctgac    2340
acctttgaag ggctctcgga ggaggccaag gactttgttt cccggttgct ggtcaaagag    2400
aagagctgca gaatgagtgc cacacagtgc ctgaaacacg agtggctgaa taatttgcct    2460
gccaaagctt caagatccaa aactcgtctc aaatcccaac tactgctgca gaaatacata    2520
gctcaaagaa aatggaagaa acatttctat gtggtgactg ctgccaacag gttaaggaaa    2580
tttccaactt ctccctaatc ttcaactctg ctaagactgg agatctggat ccctcgagtc    2640
tagagtcg                                                             2648

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gactcgagtc gacatcgatt tttttttttt ttttt                               35

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
atgtcaggag tttcagagga                                                20

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
cttgaattct cacagtgacg tatcgatgat                                     30

<210> SEQ ID NO 8
<211> LENGTH: 660
<212> TYPE: DNA
<213> ORGANISM: Artificial Sequence
<220> FEATURE:
<223> OTHER INFORMATION: synthetic template DNA used to sythesize
      neukinase DNA probe

<400> SEQUENCE: 8
atgtcaggag tttcagagga ggatccagag ggtctgggcc cccagggtct gcagcgttg     60 ggcggagcct gcttagtcac cgtggacaaa aaacttaatg tgctgactga aaggtcgac    120
```

```
agactcttgc atttccaaga agatgtcaca gagaagctac agtgtgtgtg ccaaggcatg    180
gatcacctgg aacaaggtct gcatcggctg gaggcctccc aggagttggg tctggcaggg    240
cccggcagca cttccccagc cgctgctcag gccgcatggc ctgaggtcct ggagctggtg    300
agggccgtgc ggcaggaggg tgcccagcac ggtgccaggc tcgaagccct cttcaagatg    360
gtggtggctg tggacagggc tattactttg gtagggtcca caatccagaa ctccaaagtg    420
gatgatttca tcctgcaagg gaccgtgccc tggaggaaag gcagtctggc tgatggccct    480
gaggagaaca aggagcaagc agaagtggct ggagtgaagc caaagcatgt gctgaataca    540
ggaagtgtgc aagctgccac ttctagggcg ctgtgggaag agagccagaa gcaggacaca    600
cccgtgggga cagtggaggg gctgcctctc atcatcgata cgtcactgtg agaattcaag    660
```

<210> SEQ ID NO 9
<211> LENGTH: 743
<212> TYPE: DNA
<213> ORGANISM: Artificial Sequence
<220> FEATURE:
<223> OTHER INFORMATION: target sequence for probe set 1382239 in
      Affymetrix Rat expression array 230 2.0
<220> FEATURE:
<221> NAME/KEY: misc_feature
<222> LOCATION: 125, 333, 377
<223> OTHER INFORMATION: n = A,T,C or G

<400> SEQUENCE: 9

```
agttgtagga tgagcgccac acagtgcctg aaacatgagt ggttaaatca cctgattgcc     60
aaagcctcag gctccaacgt tcgcctcaga tcccaactac tgctgcagaa atatatggct    120
cagcntaaat ggaagaaaca tttccatgtg gtgactgcag tcaacaggct aagaaaattt    180
ccaacgtgtc cctaatctac aactgggcct gggagttcct gaggcgacac gcagtggtaa    240
tgtgaagaga tgactcagga ttttatggag tcaggagctt ggctgttatt gatcttattt    300
tgcaaagaat ggtggaagga agaaagagag aangaaagaa gaaaagggaa aaggaaagaa    360
gatggctacg ttgctgncct ccttgtggat gaaagtgtgt tttttttaaag ccctaggaag    420 gtcaccaggt ctaatgctgc ctcctcccca gagccctctc ttctggtaat gagagtaggc    480
acgctcagga agggcaggga atcctactt ggcctttggt caaattcaat tctaaactcg    540
tcatgattaa agaagccagt agggagggaa gcatgggaca gggaggaatt aggtctgaca    600
gtgggaagga acatgatcga aacatactgt ataacattct taaagaatta ataaaatgta    660
tttttaaagg agtcagtagg ttcgagctgc ttgctatttt agtgaaagaa gctccttttt    720
ttttcagtga gtaatagtgc aaa                                           743
```

<210> SEQ ID NO 10
<211> LENGTH: 635
<212> TYPE: DNA
<213> ORGANISM: Artificial Sequence
<220> FEATURE:
<223> OTHER INFORMATION: target sequence for probe set 1376789 in
      Affymetrix Rat expression array 230 2.0
<220> FEATURE:
<221> NAME/KEY: misc_feature
<222> LOCATION: 29, 143, 337
<223> OTHER INFORMATION: n = A,T,C or G

<400> SEQUENCE: 10

```
ggagtcagta ggttcgagct gcttgctant ttagtgaaag aagctccttt ttttttttca     60
gtgagtaata gtgcaaagat tcagaattga tcaaaatgca aactgcactc aactctgggt    120
```

```
gagtcaatcc tcccccatcc aangctcagg gagcgtctca gaacagggga cagaaagaac      180
gtaagagttg gtagatgagg aggagtccta ggggatgtct ttgagacatg acatgacttg      240
tgttggcatc aatttacaat atctttggct acctgcacaa gatcaagtcg gccaaaattc      300
cagtgaggat gggaggaaac tcctgaggcc caccccntac tggtggagct actggcaatt      360
gttggctgat gaggcaggga gaattgttct tctttaacct ctagcagtag ttgtttatgc      420
cccagtagat gctacatacc catgtgcaga tgggcagtac caattagact ggggaggtta      480
ctgatggcaa aaaataaat aaaaggagta cctgtaggta ggaaggagat ggagtggaac       540
attagggaga attgggagca ggtagatgga tatgatcgat atgcattgta ctaatgtatg      600
gagtgttcaa agaataaaaa agtcatttaa aacag                                635

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gacaccaccg cctgagtgag aac                                             23

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
ccattggagc agcagagttg aaga                                            24

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
cgcggatcca tggacacaaa gctgaacatg                                      30

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
ccttaagtca cgtggccccc accaaagcga t                                    31

<210> SEQ ID NO 15
<211> LENGTH: 321
<212> TYPE: DNA
<213> ORGANISM: Artificial Sequence
<220> FEATURE:
<223> OTHER INFORMATION: human neukinase cDNA fragment

<400> SEQUENCE: 15
atggacacaa agctgaacat gctgaacgag aaggtggacc agctcctgca cttccaagaa      60
gatgtcacag agaagttgca gagcatgtgc cgagacatgg ccacctgga gcggggcctg      120
```

```
cacaggctgg aggcctcccg ggcaccgggc ccgggcgggg ctgatggggt tccccacatt    180
gacacccagg ctgggtggcc cgaggtcctg gagctggtga gggccatgca gcaggatgcg    240
gcccagcacg gtgccaggct ggaggccctc ttcaggatgg tggctgcggt ggacagggcc    300
atcgctttgg tgggggccac g                                              321
```

<210> SEQ ID NO 16
<211> LENGTH: 107
<212> TYPE: PRT
<213> ORGANISM: Homo sapiens

<400> SEQUENCE: 16

```
Met Asp Thr Lys Leu Asn Met Leu Asn Glu Lys Val Asp Gln Leu Leu
1               5                   10                  15

His Phe Gln Glu Asp Val Thr Glu Lys Leu Gln Ser Met Cys Arg Asp
            20                  25                  30

Met Gly His Leu Glu Arg Gly Leu His Arg Leu Glu Ala Ser Arg Ala
        35                  40                  45

Pro Gly Pro Gly Gly Ala Asp Gly Val Pro His Ile Asp Thr Gln Ala
    50                  55                  60

Gly Trp Pro Glu Val Leu Glu Leu Val Arg Ala Met Gln Gln Asp Ala
65                  70                  75                  80

Ala Gln His Gly Ala Arg Leu Glu Ala Leu Phe Arg Met Val Ala Ala
                85                  90                  95

Val Asp Arg Ala Ile Ala Leu Val Gly Ala Thr
            100                 105
```

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17

```
gggaattcca tatggcacct aagaaagcaa agaa                                 34
```

<210> SEQ ID NO 18
<211> LENGTH: 31
<212> TYPE: DNA
<213> ORGANISM: Artificial Sequence
<220> FEATURE:
<223> OTHER INFORMATION: Primer

<400> SEQUENCE: 18

```
ccgctcgagg tccttctctt ctccgtgggt g                                    31
```

<210> SEQ ID NO 19
<211> LENGTH: 166
<212> TYPE: PRT
<213> ORGANISM: Homo sapiens

<400> SEQUENCE: 19

```
Met Ala Pro Lys Lys Ala Lys Lys Arg Ala Gly Gly Ala Asn Ser Asn
1               5                   10                  15

Val Phe Ser Met Phe Glu Gln Thr Gln Ile Gln Glu Phe Lys Glu Ala
            20                  25                  30

Phe Thr Ile Met Asp Gln Asn Arg Asp Gly Phe Ile Asp Lys Asn Asp
        35                  40                  45
```

```
Leu Arg Asp Thr Phe Ala Ala Leu Gly Arg Val Asn Val Lys Asn Glu
    50                  55                  60

Glu Ile Asp Glu Met Ile Lys Glu Ala Pro Gly Pro Ile Asn Phe Thr
65                  70                  75                  80

Val Phe Leu Thr Met Phe Gly Glu Lys Leu Lys Gly Ala Asp Pro Glu
                85                  90                  95

Glu Thr Ile Leu Asn Ala Phe Lys Val Phe Asp Pro Glu Gly Lys Gly
            100                 105                 110

Val Leu Lys Ala Asp Tyr Val Arg Glu Met Leu Thr Thr Gln Ala Glu
        115                 120                 125

Arg Phe Ser Lys Glu Val Asp Gln Met Phe Ala Ala Phe Pro Pro
    130                 135                 140

Asp Val Thr Gly Asn Leu Asp Tyr Lys Asn Leu Val His Ile Ile Thr
145                 150                 155                 160

His Gly Glu Glu Lys Asp
                165
```

```
<210> SEQ ID NO 20
<211> LENGTH: 48
<212> TYPE: DNA
<213> ORGANISM: Homo sapiens

<400> SEQUENCE: 20
catcatctgg ttccgcgtgg atctatgtca ggaacctcca aggagagt            48

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21
cggaattccc attggagcag cagagttgaa g                               31

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
cgggatccat gcatcatcat catcatcatc tggttccgcg t                    41

<210> SEQ ID NO 23
<211> LENGTH: 17
<212> TYPE: DNA
<213> ORGANISM: Artificial Sequence
<220> FEATURE:
<223> OTHER INFORMATION: Primer

<400> SEQUENCE: 23
gttttcccag tcacgac                                               17

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
```

```
cggaattccc attggagcag cagagttgaa ga                                         32
```

<210> SEQ ID NO 25
<211> LENGTH: 819
<212> TYPE: PRT
<213> ORGANISM: Homo sapiens

<400> SEQUENCE: 25

| Met | Ser | Gly | Thr | Ser | Lys | Glu | Ser | Leu | Gly | His | Gly | Gly | Leu | Pro | Gly |
|---|---|---|---|---|---|---|---|---|---|---|---|---|---|---|---|
| 1 | | | | 5 | | | | | 10 | | | | | 15 | |

Leu Gly Lys Thr Cys Leu Thr Thr Met Asp Thr Lys Leu Asn Met Leu
                20                  25                  30

Asn Glu Lys Val Asp Gln Leu Leu His Phe Gln Glu Asp Val Thr Glu
            35                  40                  45

Lys Leu Gln Ser Met Cys Arg Asp Met Gly His Leu Glu Arg Gly Leu
 50                  55                  60

His Arg Leu Glu Ala Ser Arg Ala Pro Gly Pro Gly Gly Ala Asp Gly
 65                  70                  75                  80

Val Pro His Ile Asp Thr Gln Ala Gly Trp Pro Glu Val Leu Glu Leu
                85                  90                  95

Val Arg Ala Met Gln Gln Asp Ala Ala Gln His Gly Ala Arg Leu Glu
                100                 105                 110

Ala Leu Phe Arg Met Val Ala Ala Val Asp Arg Ala Ile Ala Leu Val
            115                 120                 125

Gly Ala Thr Phe Gln Lys Ser Lys Val Ala Asp Phe Leu Met Gln Gly
            130                 135                 140

Arg Val Pro Trp Arg Arg Gly Ser Pro Gly Asp Ser Pro Glu Glu Asn
145                 150                 155                 160

Lys Glu Arg Val Glu Glu Gly Gly Lys Pro Lys His Val Leu Ser
                165                 170                 175

Thr Ser Gly Leu Gln Ser Asp Ala Arg Glu Pro Gly Glu Glu Ser Gln
                180                 185                 190

Lys Ala Asp Val Leu Glu Gly Thr Ala Glu Arg Leu Pro Pro Ile Arg
            195                 200                 205

Ala Ser Gly Leu Gly Ala Asp Pro Ala Gln Ala Val Val Ser Pro Gly
    210                 215                 220

Gln Gly Asp Gly Val Pro Gly Pro Ala Gln Ala Phe Pro Gly His Leu
225                 230                 235                 240

Pro Leu Pro Thr Lys Val Glu Ala Lys Ala Pro Glu Thr Pro Ser Glu
                245                 250                 255

Asn Leu Arg Thr Gly Leu Glu Leu Ala Pro Ala Pro Gly Arg Val Asn
                260                 265                 270

Val Val Ser Pro Ser Leu Glu Val Ala Pro Gly Ala Gly Gln Gly Ala
            275                 280                 285

Ser Ser Ser Arg Pro Asp Pro Glu Pro Leu Glu Glu Gly Thr Arg Leu
    290                 295                 300

Thr Pro Gly Pro Gly Pro Gln Cys Pro Gly Pro Pro Gly Leu Pro Ala
305                 310                 315                 320

Gln Ala Arg Ala Thr His Ser Gly Gly Glu Thr Pro Pro Arg Ile Ser
                325                 330                 335

Ile His Ile Gln Glu Met Asp Thr Pro Gly Glu Met Leu Met Thr Gly
            340                 345                 350

Arg Gly Ser Leu Gly Pro Thr Leu Thr Thr Glu Ala Pro Ala Ala Ala
    355                 360                 365

```
Gln Pro Gly Lys Gln Gly Pro Pro Gly Thr Gly Arg Cys Leu Gln Ala
    370                 375                 380
Pro Gly Thr Glu Pro Gly Glu Gln Thr Pro Glu Gly Ala Arg Glu Leu
385                 390                 395                 400
Ser Pro Leu Gln Glu Ser Ser Pro Gly Gly Val Lys Ala Glu Glu
                405                 410                 415
Glu Gln Arg Ala Gly Ala Glu Pro Gly Thr Arg Pro Ser Leu Ala Arg
            420                 425                 430
Ser Asp Asp Asn Asp His Glu Val Gly Ala Leu Gly Leu Gln Gln Gly
        435                 440                 445
Lys Ser Pro Gly Ala Gly Asn Pro Glu Pro Glu Gln Asp Cys Ala Ala
    450                 455                 460
Arg Ala Pro Val Arg Ala Glu Ala Val Arg Arg Met Pro Pro Gly Ala
465                 470                 475                 480
Glu Ala Gly Ser Val Val Leu Asp Asp Ser Pro Ala Pro Pro Ala Pro
                485                 490                 495
Phe Glu His Arg Val Val Ser Val Lys Glu Thr Ser Ile Ser Ala Gly
            500                 505                 510
Tyr Glu Val Cys Gln His Glu Val Leu Gly Gly Arg Phe Gly Gln
        515                 520                 525
Val His Arg Cys Thr Glu Lys Ser Thr Gly Leu Pro Leu Ala Ala Lys
    530                 535                 540
Ile Ile Lys Val Lys Ser Ala Lys Asp Arg Glu Asp Val Lys Asn Glu
545                 550                 555                 560
Ile Asn Ile Met Asn Gln Leu Ser His Val Asn Leu Ile Gln Leu Tyr
                565                 570                 575
Asp Ala Phe Glu Ser Lys His Ser Cys Thr Leu Val Met Glu Tyr Val
            580                 585                 590
Asp Gly Gly Glu Leu Phe Asp Arg Ile Thr Asp Glu Lys Tyr His Leu
        595                 600                 605
Thr Glu Leu Asp Val Val Leu Phe Thr Arg Gln Ile Cys Glu Gly Val
    610                 615                 620
His Tyr Leu His Gln His Tyr Ile Leu His Leu Asp Leu Lys Pro Glu
625                 630                 635                 640
Asn Ile Leu Cys Val Asn Gln Thr Gly His Gln Ile Lys Ile Ile Asp
                645                 650                 655
Phe Gly Leu Ala Arg Arg Tyr Lys Pro Arg Glu Lys Leu Lys Val Asn
            660                 665                 670
Phe Gly Thr Pro Glu Phe Leu Ala Pro Glu Val Val Asn Tyr Glu Phe
        675                 680                 685
Val Ser Phe Pro Thr Asp Met Trp Ser Val Gly Val Ile Thr Tyr Met
    690                 695                 700
Leu Leu Ser Gly Leu Ser Pro Phe Leu Gly Glu Thr Asp Ala Glu Thr
705                 710                 715                 720
Met Asn Phe Ile Val Asn Cys Ser Trp Asp Phe Asp Ala Asp Thr Phe
                725                 730                 735
Glu Gly Leu Ser Glu Glu Ala Lys Asp Phe Val Ser Arg Leu Leu Val
            740                 745                 750
Lys Glu Lys Ser Cys Arg Met Ser Ala Thr Gln Cys Leu Lys His Glu
        755                 760                 765
Trp Leu Asn Asn Leu Pro Ala Lys Ala Ser Arg Ser Lys Thr Arg Leu
    770                 775                 780
```

```
Lys Ser Gln Leu Leu Leu Gln Lys Tyr Ile Ala Gln Arg Lys Trp Lys
785                 790                 795                 800

Lys His Phe Tyr Val Val Thr Ala Ala Asn Arg Leu Arg Lys Phe Pro
                805                 810                 815

Thr Ser Pro

<210> SEQ ID NO 26
<211> LENGTH: 596
<212> TYPE: PRT
<213> ORGANISM: Homo sapiens

<400> SEQUENCE: 26

Met Ala Thr Glu Asn Gly Ala Val Glu Leu Gly Ile Gln Asn Pro Ser
 1               5                  10                  15

Thr Asp Lys Ala Pro Lys Gly Pro Thr Gly Glu Arg Pro Leu Ala Ala
                20                  25                  30

Gly Lys Asp Pro Gly Pro Pro Asp Pro Lys Lys Ala Pro Asp Pro Pro
            35                  40                  45

Thr Leu Lys Lys Asp Ala Lys Ala Pro Ala Ser Glu Lys Gly Asp Gly
50                  55                  60

Thr Leu Ala Gln Pro Ser Thr Ser Ser Gln Gly Pro Lys Gly Glu Gly
65                  70                  75                  80

Asp Arg Gly Gly Gly Pro Ala Glu Gly Ser Ala Gly Pro Pro Ala Ala
                85                  90                  95

Leu Pro Gln Gln Thr Ala Thr Pro Glu Thr Ser Val Lys Lys Pro Lys
            100                 105                 110

Ala Glu Gln Gly Ala Ser Gly Ser Gln Asp Pro Gly Lys Pro Arg Val
            115                 120                 125

Gly Lys Lys Ala Ala Glu Gly Gln Ala Ala Arg Arg Gly Ser Pro
130                 135                 140

Ala Phe Leu His Ser Pro Ser Cys Pro Ala Ile Ile Ser Ser Glu
145                 150                 155                 160

Lys Leu Leu Ala Lys Lys Pro Pro Ser Glu Ala Ser Glu Leu Thr Phe
                165                 170                 175

Glu Gly Val Pro Met Thr His Ser Pro Thr Asp Pro Arg Pro Ala Lys
            180                 185                 190

Ala Glu Glu Gly Lys Asn Ile Leu Ala Glu Ser Gln Lys Glu Val Gly
            195                 200                 205

Glu Lys Thr Pro Gly Gln Ala Gly Gln Ala Lys Met Gln Gly Asp Thr
210                 215                 220

Ser Arg Gly Ile Glu Phe Gln Ala Val Pro Ser Glu Lys Ser Glu Val
225                 230                 235                 240

Gly Gln Ala Leu Cys Leu Thr Arg Glu Glu Asp Cys Phe Gln Ile
                245                 250                 255

Leu Asp Asp Cys Pro Pro Pro Ala Pro Phe Pro His Arg Met Val
            260                 265                 270

Glu Leu Arg Thr Gly Asn Val Ser Ser Glu Phe Ser Met Asn Ser Lys
            275                 280                 285

Glu Ala Leu Gly Gly Lys Phe Gly Ala Val Cys Thr Cys Met Glu
290                 295                 300

Lys Ala Thr Gly Leu Lys Leu Ala Ala Lys Val Ile Lys Lys Gln Thr
305                 310                 315                 320

Pro Lys Asp Lys Glu Met Val Leu Leu Glu Ile Glu Val Met Asn Gln
                325                 330                 335
```

-continued

```
Leu Asn His Arg Asn Leu Ile Gln Leu Tyr Ala Ala Ile Glu Thr Pro
            340                 345                 350
His Glu Ile Val Leu Phe Met Glu Tyr Ile Glu Gly Gly Glu Leu Phe
            355                 360                 365
Glu Arg Ile Val Asp Glu Asp Tyr His Leu Thr Glu Val Asp Thr Met
    370                 375                 380
Val Phe Val Arg Gln Ile Cys Asp Gly Ile Leu Phe Met His Lys Met
385                 390                 395                 400
Arg Val Leu His Leu Asp Leu Lys Pro Glu Asn Ile Leu Cys Val Asn
                405                 410                 415
Thr Thr Gly His Leu Val Lys Ile Ile Asp Phe Gly Leu Ala Arg Arg
                420                 425                 430
Tyr Asn Pro Asn Glu Lys Leu Lys Val Asn Phe Gly Thr Pro Glu Phe
            435                 440                 445
Leu Ser Pro Glu Val Val Asn Tyr Asp Gln Ile Ser Asp Lys Thr Asp
    450                 455                 460
Met Trp Ser Met Gly Val Ile Thr Tyr Met Leu Leu Ser Gly Leu Ser
465                 470                 475                 480
Pro Phe Leu Gly Asp Asp Asp Thr Glu Thr Leu Asn Asn Val Leu Ser
                485                 490                 495
Gly Asn Trp Tyr Phe Asp Glu Glu Thr Phe Glu Ala Val Ser Asp Glu
            500                 505                 510
Ala Lys Asp Phe Val Ser Asn Leu Ile Val Lys Asp Gln Arg Ala Arg
            515                 520                 525
Met Asn Ala Ala Gln Cys Leu Ala His Pro Trp Leu Asn Asn Leu Ala
530                 535                 540
Glu Lys Ala Lys Arg Cys Asn Arg Arg Leu Lys Ser Gln Ile Leu Leu
545                 550                 555                 560
Lys Lys Tyr Leu Met Lys Arg Arg Trp Lys Lys Asn Phe Ile Ala Val
                565                 570                 575
Ser Ala Ala Asn Arg Phe Lys Lys Ile Ser Ser Ser Gly Ala Leu Met
            580                 585                 590
Ala Leu Gly Val
            595
```

NEUKINASE, A DOWNSTREAM PROTEIN OF NEUREGULIN

RELATED APPLICATIONS

This application claims the benefit of U.S. Provisional Application No. 60/839,388,filed Aug. 21, 2006, and U.S. Provisional Application No. 60/921,655, filed Apr. 2, 2007, the contents of which are hereby incorporated by reference in their entireties.

1. FIELD OF THE INVENTION

The present invention relates to neukinase, a downstream protein kinase in the neuregulin signaling pathway. In certain aspects, the present invention provides isolated neukinase-encoding nucleic acids, neukinase polypeptides, oligonucleotides that hybridize to neukinase nucleic acids, and expression vectors containing neukinase-encoding sequences. The present invention further provides isolated host cells, antibodies, transgenic non-human animals, compositions, and kits relating to neukinase. In other aspects, the present invention further provides methods of identifying predisposition to cardiac dysfunction, methods of detecting the presence of neukinase, neukinase nucleic acid, methods of screening for agents which affect neukinase activity, and methods of modulating neukinase activity.

2. BACKGROUND OF THE INVENTION

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects. Additional limitations are associated with other options for preventing or treating heart failure. For example, heart transplantation is clearly more expensive and invasive than drug treatment, and it is further limited by the availability of donor hearts. Use of mechanical devices, such as biventricular pacemakers, are similarly invasive and expensive. Thus, there has been a need for new therapies given the deficiencies in current therapies.

One promising new therapy involves administration of neuregulin (hereinafter referred to as "NRG") to a patient suffering from, or at risk of developing, heart failure. NRGs comprise a family of structurally related growth and differentiation factors that include NRG 1, NRG2, NRG3 and NRG4 and isoforms thereof. For example, over 15 distinct isoforms of NRG1 have been identified and divided into two large groups, known as α- and β-types, on the basis of differences in the sequence of their essential epidermal growth factor (EGF)-like domains. It has been shown that the EGF-like domains of NRG1, ranging in size from 50 to 64-amino acids, are sufficient to bind to and activate these receptors. Previous studies have shown that neuregulin-1β (NRG-1β) can bind directly to ErbB3 and ErbB4 with high affinity.

Recent studies highlight the roles of NRG-1β, ErbB2 and ErbB4 in the cardiovascular development as well as in the maintenance of adult normal heart function. NRG-1β has been shown to enhance sarcomere organization in adult cardiomyocytes. The short-term administration of a recombinant NRG-1β EGF-like domain significantly improves or protects against deterioration in myocardial performance in three distinct animal models of heart failure. More importantly, NRG-1β significantly prolongs survival of animals experiencing heart failure. These effects make NRG-1β promising as a broad spectrum therapeutic or lead compound for heart failure due to a variety of common diseases.

However, there is a need for additional methods of affecting neuregulin signal transduction and/or activation of downstream neuregulin signaling targets which can be used in a clinical setting for the prevention, treatment or delay of heart failure and/or cardiac hypertrophy.

3. SUMMARY OF THE INVENTION

The present invention is based in part on the discovery of a novel protein kinase, termed neukinase, which exhibits structural similarity to skeletal muscle myosin light chain kinase and acts as a downstream component in the neuregulin signaling pathway. A neukinase cDNA has been cloned and sequenced, and a neukinase amino acid sequence has been determined. The upstream regulatory protein, neuregulin, enhances neukinase expression and/or phosphorylation, which in turn increases phosphorylation of the downstream target myosin light chain. As neukinase is highly expressed in heart tissue, the present invention provides a new mechanism underlying the prophylactic and therapeutic effects of neuregulin on the heart, and identifies a new target for treating cardiovascular disease.

Accordingly, in a first aspect, the present invention provides an isolated polypeptide comprising an amino acid sequence having at least 70% identity to SEQ ID NO:1, wherein the polypeptide is capable of phosphorylating myosin light chain. In another aspect, the present invention provides an isolated polypeptide comprising an amino acid sequence having at least 70% identity to SEQ ID NO:2, wherein the polypeptide is capable of phosphorylating myosin light chain. In certain embodiments, the isolated polypeptide is capable of phosphorylating the myosin light chain of cardiac myosin. In certain embodiments, the isolated polypeptide is capable of phosphorylating the myosin light chain of cardiac myosin of a mammal, which includes but is not limited to, a rat, mouse, or human.

In one embodiment, the isolated polypeptide comprises the amino acid sequence of SEQ ID NO:1. In another embodiment, the isolated polypeptide comprises the amino acid sequence of SEQ ID NO:2. In some embodiments, the isolated polypeptide comprises the amino acid sequence of SEQ ID NO:25.

In another aspect, the invention provides an isolated nucleic acid encoding a polypeptide comprising an amino acid sequence having at least 70% identity to SEQ ID NO:1. In certain embodiments, the isolated nucleic acid encodes a polypeptide comprising the amino acid sequence of SEQ ID NO:1. In certain embodiments, the isolated nucleic acid comprises a nucleic acid sequence having at least 70% identity to at least about 500 contiguous nucleotides selected from SEQ ID NO:3 or the complement thereof. In certain embodiments, the isolated nucleic acid comprises at least about 500 nucleotides selected from the nucleic acid sequence of SEQ ID NO:3, or the complement thereof. In a particular embodiment, the isolated nucleic acid comprises the nucleic acid sequence of SEQ ID NO:3, or the complement thereof.

In another aspect, the invention provides an isolated nucleic acid encoding a polypeptide comprising an amino acid sequence having at least 70% identity to SEQ ID NO:2. In certain embodiments, the isolated nucleic acid encodes a polypeptide comprising the amino acid sequence of SEQ ID NO:2. In some embodiments, the isolated nucleic acid encodes a polypeptide comprising an amino acid sequence having at least 70% identity to SEQ ID NO:25. In certain embodiments, the isolated nucleic acid encodes a polypeptide comprising the amino acid sequence of SEQ ID NO:25. In certain embodiments, the isolated nucleic acid comprises a nucleic acid sequence having at least 70% identity to at least about 500 contiguous nucleotides selected from SEQ ID NO:4 or the complement thereof. In certain embodiments, the isolated nucleic acid comprises at least about 500 nucleotides selected from the nucleic acid sequence of SEQ ID NO:4, or the complement thereof. In a particular embodiment, the isolated nucleic acid comprises the nucleic acid sequence of SEQ ID NO:4, or the complement thereof.

In another aspect, the invention provides an isolated oligonucleotide comprising at least about 10 consecutive nucleotides of SEQ ID NO:3 or its complementary strand. In another aspect, the invention provides an isolated oligonucleotide comprising at least about 10 consecutive nucleotides of SEQ ID NO:4 or its complementary strand. In certain embodiments, the isolated oligonucleotide comprises the nucleic acid sequence of SEQ ID NO:5 or SEQ ID NO:6.

In another aspect, the invention provides a vector comprising an isolated nucleic acid encoding a polypeptide, wherein the encoded polypeptide is capable of phosphorylating myosin light chain. In certain embodiments, the vector comprises at least about 500 nucleotides selected from the nucleic acid sequence of SEQ ID NO:3. In certain embodiments, the vector comprises the nucleic acid sequence of SEQ ID NO:3. In certain embodiments, the vector comprises at least about 500 nucleotides selected from the nucleic acid sequence of SEQ ID NO:4. In certain embodiments, the vector comprises the nucleic acid sequence of SEQ ID NO:4. In a particular embodiment, the neukinase nucleic acid sequence in the vector is operably linked to a transcriptional regulatory sequence. In certain embodiments, the vector is selected from the group comprising a plasmid, a cosmid, a virus, and a bacteriophage. In certain embodiments, the vector expresses a polypeptide comprising SEQ ID NO:1 in a cell transformed with said vector. In certain embodiments, the vector expresses a polypeptide comprising SEQ ID NO:2 in a cell transformed with said vector. In certain embodiments, the vector expresses a polypeptide comprising SEQ ID NO:25 in a cell transformed with said vector.

In another aspect, the invention provides an isolated host cell comprising a neukinase nucleic acid according to the present invention. In another aspect, the invention provides an isolated host cell comprising a vector that expresses neukinase. In certain embodiments, the isolated host cell is a neonatal rat ventricular myocyte. In certain embodiments, the isolated host cell is an H9c2(2-1) cell.

In another aspect, the invention provides an antibody that specifically binds to a polypeptide comprising an amino acid sequence of SEQ ID NO:1. In another aspect, the invention provides an antibody that specifically binds to a polypeptide comprising an amino acid sequence of SEQ ID NO:2. In some embodiments, the antibody specifically binds to a neukinase polypeptide comprising an amino acid sequence of SEQ ID NO:25. In certain embodiments, the antibody is a polyclonal, monoclonal, single chain monoclonal, recombinant, chimeric, humanized, mammalian, or human antibody.

In another aspect, the invention provides a transgenic non-human animal, which expresses a nucleic acid encoding neukinase polypeptide. In certain embodiments, the transgenic non-human animal neukinase polypeptide comprises the amino acid sequence of SEQ ID NO:1. In certain embodiments, the transgenic non-human animal neukinase polypeptide comprises the amino acid sequence of SEQ ID NO:2. In certain embodiments, the transgenic non-human animal neukinase polypeptide comprises the amino acid sequence of SEQ ID NO:25. In a particular embodiment, the transgenic non-human animal over- or under-expresses neukinase polypeptide. In one embodiment, the transgenic non-human animal comprises a nucleic acid having at least 70% identity to SEQ ID NO:3, or the complement thereof. In another embodiment, the transgenic non-human animal of comprises a nucleic acid having at least 70% identity to SEQ ID NO:4, or the complement thereof. In certain embodiments, the transgenic non-human animal is a mammal, including, but not limited to, a mouse, rat, rabbit, hamster, or sheep.

In another aspect, the invention provides a transgenic non-human animal whose germ cells comprise a homozygous null mutation in the endogenous nucleic acid sequence encoding neukinase, wherein the mutation is created by insertion of, e.g., a neomycin cassette, in reverse orientation to neukinase transcription and wherein said mutation has been introduced into said animal by homologous recombination in an embryonic stem cell such that said animal does not express a functional neukinase polypeptide. In certain embodiments, the transgenic non-human animal is fertile and transmits said null mutation to its offspring. In particular embodiments, the transgenic non-human animal is a mammal, including, but not limited to, a mouse, rat, rabbit, hamster, or sheep.

In another aspect, the invention provides a method of screening for agents that affect neukinase activity, comprising: a) administering said agent to a cell that expresses a neukinase polypeptide; and b) assessing a biological activity of the neukinase in the cell. In certain embodiments, the biological activity is selected from the group consisting of autoinhibition, phosphorylation of cardiac myosin, and expression of neukinase.

In another aspect, the invention provides a method of screening for agents that affect neukinase activity, comprising: a) administering said agent to a transgenic non-human animal according to the present invention; and b) assessing the animal for an alteration in cardiac function affected by said agent. In certain embodiments, the cardiac function is selected from the group consisting of interventricular septum size, left ventricle end diastolic dimension, posterior wall thickness, left ventricle end systolic dimension, ejection fraction, fractional shortening, and cardiac cycle.

In another aspect, the invention provides a method of detecting the presence of the neukinase nucleic acid in a sample, comprising: (a) contacting the sample with a nucleic acid that hybridizes to the neukinase nucleic acid; and (b) determining whether the nucleic acid binds to a nucleic acid in the sample.

In another aspect, the invention provides a method for identifying whether a subject is genetically predisposed to cardiac dysfunction, comprising, detecting in a biological sample from the subject, a neukinase gene associated with cardiac dysfunction. In certain embodiments, the cardiac dysfunction is hypertrophic cardiomyopathy or heart failure.

In another aspect, the invention provides a composition comprising a neukinase polypeptide of the invention and a pharmaceutically acceptable carrier. In another aspect, the invention provides a composition comprising a polypeptide having an amino acid sequence that comprises SEQ ID NO:1 and a pharmaceutically acceptable carrier. In another aspect, the invention provides a composition comprising a polypeptide having an amino acid sequence that comprises SEQ ID NO:2 and a pharmaceutically acceptable carrier. In some embodiments, the composition comprises a polypeptide having an amino acid sequence that comprises SEQ ID NO:25 and a pharmaceutically acceptable carrier.

In another aspect, the invention provides a composition comprising a neukinase-encoding nucleic acid of the invention and a pharmaceutically acceptable carrier. In another aspect, the invention provides a composition comprising a polynucleotide encoding a polypeptide having an amino acid sequence that comprises SEQ ID NO:1 and a pharmaceutically acceptable carrier. In certain embodiments, the polynucleotide comprises a nucleotide sequence of SEQ ID NO:3. In another aspect, the invention provides a composition comprising a polynucleotide encoding a polypeptide having an amino acid sequence that comprises SEQ ID NO:2 and a pharmaceutically acceptable carrier. In some embodiments, the composition comprises a polynucleotide encoding a polypeptide having an amino acid sequence that comprises SEQ ID NO:25 and a pharmaceutically acceptable carrier. In certain embodiments, the polynucleotide comprises a nucleotide sequence of SEQ ID NO:4.

In another aspect, the invention provides a kit comprising i) an isolated oligonucleotide comprising at least 10 consecutive nucleotides of SEQ ID NO:3, or its complementary strand; and ii) a container. In certain embodiments, the kit contains the oligonucleotide which comprises at least 15 consecutive nucleotides of SEQ ID NO:3 or its complementary strand.

In another aspect, the invention provides a kit comprising i) an isolated oligonucleotide comprising at least 10 consecutive nucleotides of SEQ ID NO:4, or its complementary strand; and ii) a container. In certain embodiments, the kit contains the oligonucleotide which comprises at least 15 consecutive nucleotides of SEQ ID NO:4, or its complementary strand.

In another aspect, the invention provides a method of modulating neukinase activity, which comprises inhibiting the autoinhibitory domain of the neukinase polypeptide with a compound that inhibits such a domain. In certain embodiments, the compound is $Ca^{2+}$/calmodulin.

4. BRIEF DESCRIPTION OF THE DRAWINGS

FIG. 1 shows Northern blot analysis of rat neukinase mRNA expression in rat heart, brain, spleen, lung, liver, skeletal muscle, kidney and testis tissues. Hybridization with a β-actin specific probe serves as a loading control.

Figure 2:
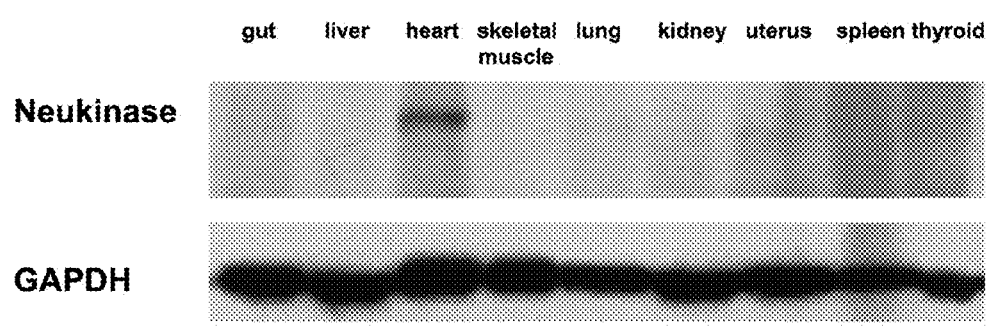

FIG. 2 shows Western blot analysis of human neukinase protein expression in human gut, liver, heart, skeletal muscle, lung, kidney, uterus, spleen and thyroid tissues. The membrane was probed with an anti-neukinase rabbit polyclonal antibody. Probing with a anti-GAPDH antibody serves as a loading control.

Figure 3:
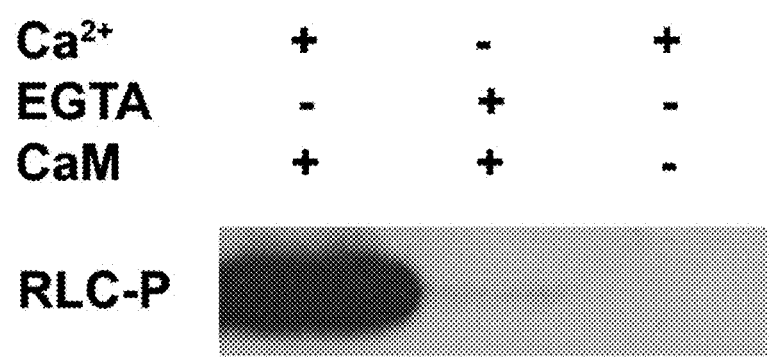

FIG. 3 shows the levels of phosphorylated regulatory myosin light chain (RLC-P) in a cell-free neukinase activity assay. Recombinantly expressed neukinase and RLC were co-incubated in the presence or absence of $Ca^{2+}$ and calmodulin (CaM), −/+ EGTA. RLC phosphorylation was assessed by Western blot analysis using anti-RLC-P antibody as probe.

Figure 4:
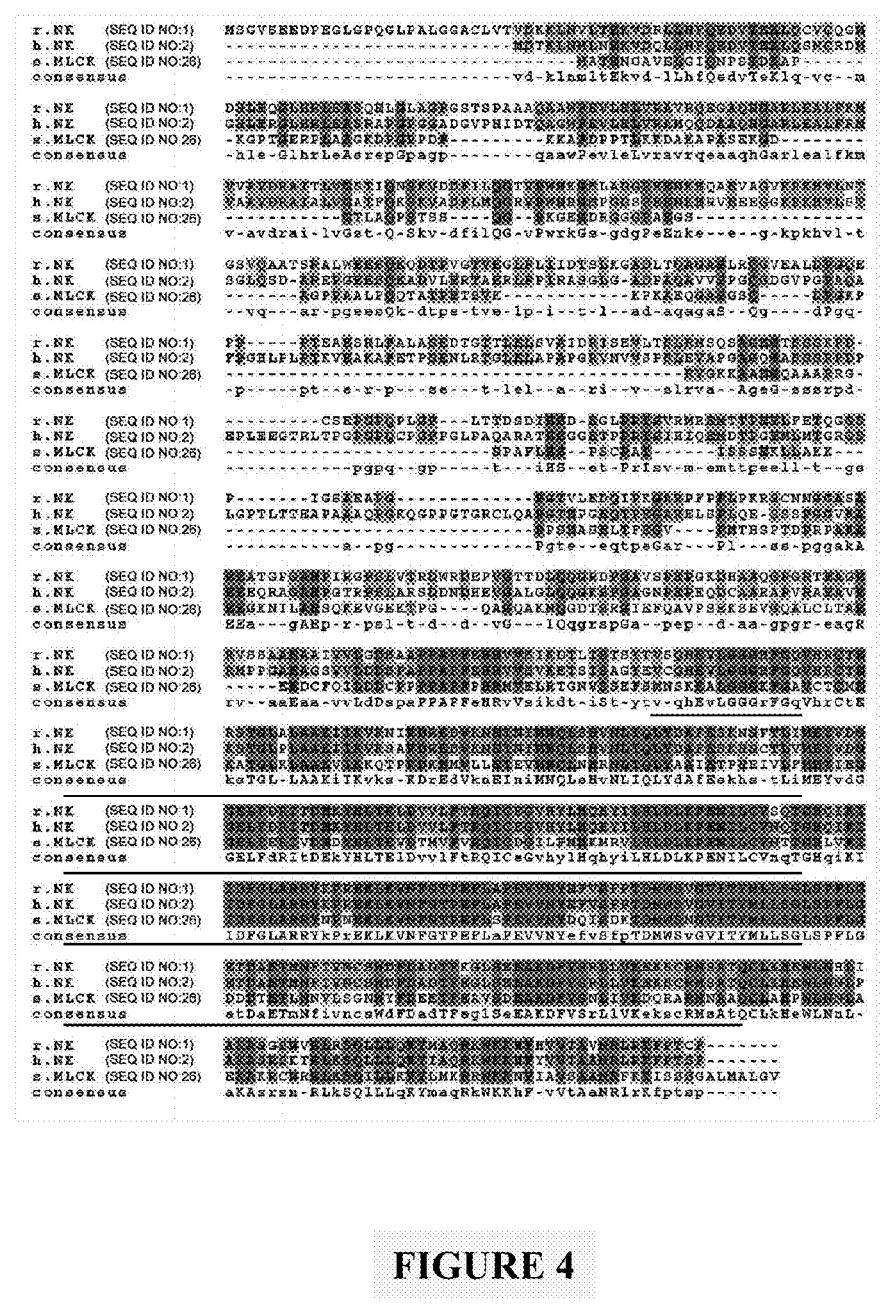

FIG. 4 shows an amino acid sequence alignment of rat neukinase (r.NK), human neukinase (h.NK) and human skeletal myosin light chain kinase (s.MLCK; accession no. NP_149109). Darkly shaded boxes represent completely conserved residues, moderately shaded boxes represent identical residues, and lightly shaded boxes represent similar residues. The serine/threonine protein kinase catalytic domain of skeletal myosin light chain kinase is underlined (residues 291-540).

5. DETAILED DESCRIPTION OF THE INVENTION

This disclosure provides, for the first time, an isolated cDNA molecule which, when transfected into cells can produce neukinase protein. Neukinase protein is believed to be linked to, inter alia, cardiac dysfunction, cardiac hypertrophy and certain forms of cardiomyopathy such as hypertrophic cardiomyopathy and mid-cavitary ventricular hypertrophy. This disclosure provides the molecule, the nucleotide sequence of this cDNA and the amino acid sequence of neukinase protein encoded by this cDNA.

Having herein provided the nucleotide sequence of the neukinase cDNA, correspondingly provided are the complementary DNA strands of the cDNA molecule, and DNA molecules which hybridize under stringent conditions to neukinase cDNA molecule, or its complementary strand. Such hybridizing molecules include DNA molecules differing only by minor sequence changes, including nucleotide substitutions, deletions and additions. Also comprehended by this invention are isolated oligonucleotides comprising at least a portion of the cDNA molecule or its complementary strand. These oligonucleotides can be employed as effective DNA hybridization probes or primers for use in the polymerase chain reaction. Such probes and primers are particularly useful in the screening and diagnosis of persons genetically predisposed to hypertrophic cardiomyopathy and other forms of cardiac dysfunction, as the result of neukinase gene mutations.

Recombinant DNA vector comprising the disclosed DNA molecules, and transgenic host cells containing such recombinant vectors, are also provided. Disclosed embodiments also include transgenic nonhuman animals which over- or under-express neukinase protein, or over- or under-express fragments or variants of neukinase protein.

For clarity of disclosure, and not by way of limitation, the detailed description of the invention hereinafter is divided into the subsections that follow. All publications mentioned herein are incorporated by reference to disclose and describe the methods and/or materials in connection with which the publications are cited.

5.1 Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an," and "the" mean "at least one" or "one or more" unless the context clearly dictates otherwise.

As used herein, "neuregulin" or "NRG" used in the present invention refers to proteins or peptides that can bind and activate ErbB2, ErbB3, ErbB4 or combinations thereof, including but not limited to all neuregulin isoforms, neuregulin EGF domain alone, polypeptides comprising neuregulin EGF-like domain, neuregulin mutants or derivatives, and any kind of neuregulin-like gene products that also activate the above receptors as described in detail below. In preferred embodiments, neuregulin used in the present invention binds to and activates ErbB2/ErbB4 or ErbB2/ErbB3 heterodimers. Neuregulin also includes NRG-1, NRG-2, NRG-3, and NRG-4 proteins, peptides, fragments and compounds that mimic the activities of neuregulin. Neuregulin used in the present invention can activate the above ErbB receptors and modulate their biological reactions, e.g., stimulate breast cancer cell differentiation and milk protein secretion; induce the differentiation of neural crest cell into Schwann cell; stimulate acetylcholine receptor synthesis in skeletal muscle cell; and/or improve cardiocyte differentiation, survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th ed., The Benjamin/Cummings Pub. Co., p. 224 (1987)). Neuregulin protein encompasses a neuregulin protein and peptide. Neuregulin nucleic acid encompasses neuregulin nucleic acid and neuregulin oligonucleotides.

As used herein, "epidermal growth factor-like domain" or "EGF-like domain" refers to a polypeptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., *Science,* 256: 1205-1210 (1992); U.S. Pat. Nos. 5,530,109 and 5,716,930; Hijazi et al., *Int. J. Oncol.,* 13:1061-1067 (1998); Chang et al., *Nature,* 387:509-512 (1997); Carraway et al., *Nature,* 387:512-516 (1997); Higashiyama et al., *J. Biochem.,* 122: 675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro, as described in U.S. Pat. No. 5,834,229.

As used herein, "neukinase" refers to proteins or peptides which have an amino acid sequence that is identical to SEQ ID NO:1, SEQ ID NO:2, or SEQ ID NO:25, as well as proteins sharing sequence similarity, e.g., 70%, 75%, 80%, 85%, 90%, 95%, or greater percent identity, with the amino acid sequence of SEQ ID NO:1, SEQ ID NO:2, or SEQ ID NO:25. Further, these proteins have a biological activity in common with the polypeptide having the amino acid sequence of SEQ ID NO:1, SEQ ID NO:2 or SEQ ID NO:25, including, but not limited to, antigenic cross-reactivity, autoinhibition, phosphorylation activity, and the like. It is also contemplated that a neukinase protein can have one or more conservative or non-conservative amino acid substitutions, or additions or deletions from the amino acid sequence of SEQ ID NO:1, SEQ ID NO:2 or SEQ ID NO:25 so long as the protein having such sequence alteration shares a biological activity as described above with the polypeptide of SEQ ID NO:1, SEQ ID NO:2 or SEQ ID NO:25. Neukinase also includes proteins or peptides expressed from different mutations, different spliced forms and various sequence polymorphisms of the neukinase gene.

As used herein, "functional fragments and variants of neukinase" refer to those fragments and variants that maintain one or more functions of neukinase. It is recognized that the gene or cDNA encoding neukinase can be considerably mutated without materially altering one or more neukinase functions. First, the genetic code is well-known to be degenerate, and thus different codons may encode the same amino acids. Second, even where an amino acid substitution is introduced, the mutation can be conservative and have no material impact on the essential functions of neukinase. Third, part of the neukinase polypeptide can be deleted without impairing or eliminating all of its functions. Fourth, insertions or additions can be made in neukinase, for example, adding epitope tags, without impairing or eliminating its functions. Other modifications can be made without materially impairing one or more functions of neukinase, for example, in vivo or in vitro chemical and biochemical modifications which incorporate unusual amino acids. Such modifications include, for example, acetylation, carboxylation, phosphorylation, glycosylation, ubiquination, labeling with radionuclides, and various enzymatic modifications, as will be readily appreciated by those skilled in the art. A variety of methods for labeling proteins and substituents or labels useful for such purposes are well known in the art, and include radioactive isotopes such as ligands which bind to labeled antiligands (e.g., antibodies), fluorophores, chemiluminescent agents, enzymes, and antiligands. Functional fragments and variants can be of varying length. For example, some fragments have at least 10, 25, 50, 75, 100, or 200 or more amino acid residues.

As used herein, "myosin light chain" refers to an about 18 kDa protein which associates with the myosin heavy chain and participates in the regulation of myosin's force-generating ATPase activity. There are two major groupings of MLC: MLC1, sometimes referred to as the essential myosin light chain, abbreviated ELC; and MLC2, sometimes referred to as the regulatory myosin light chain, abbreviated RLC. RLC is the primary biological target of myosin light chain kinase (MLCK)-mediated phosphorylation. When phosphorylated by MLCK the phosphorylated form of RLC is abbreviated of RLC-P. Isoforms of ELC and RLC existing in skeletal, smooth, and cardiac muscle have been described. As an example, the human cardiac RLC gene and cDNA are described by Macera et al., *Genomics* 13: 829-31 (1992); (GenBank accession no. NM00432).

As used herein, a "functional fragment or variant of myosin light chain" refers to a polypeptide which is capable of being phosphorylated by a protein having myosin light chain kinase biological activity. It includes any polypeptide six or more amino acid residues in length which is capable of being phosphorylated by a protein having myosin light chain kinase biological activity.

As used herein, "myosin light chain kinase biological activity" refers to the in vitro or in vivo enzymatic ability of a polypeptide or protein to mediate covalent incorporation of a phosphate into a regulatory myosin light chain. The term encompasses such enzymatic activity observed with any isoform of MLCK (for example, smooth muscle, skeletal muscle, and cardiac MLCK isoforms), as well as such enzymatic activity observed with fragments and variants of MLCK isoforms (for example, naturally occurring mutants; mutations, insertions and deletions introduced through recombinant DNA techniques; and fragments generated by proteolysis).

As used herein, "protein" is synonymous with "polypeptide" or "peptide" unless the context clearly dictates otherwise.

As used herein, a "neukinase gene" refers to a gene that encodes neukinase as defined herein. A mutation of neukinase gene includes nucleotide sequence changes, additions or deletions, including deletion of large portions or the entire neukinase gene, or duplications of all or substantially all of the gene. Alternatively, genetic expression of neukinase can be deregulated such that neukinase is over or under expressed. The term "neukinase gene" is understood to include the various sequence polymorphisms and allelic variations that exist within the population. This term relates primarily to an isolated coding sequence, but can also include some or all of the flanking regulatory elements and/or intron sequences. The RNA transcribed from a mutant neukinase gene is mutant neukinase messenger RNA.

As used herein, "neukinase cDNA" refers to a cDNA molecule which, when transfected or otherwise introduced into cells, expresses the neukinase protein. The neukinase cDNA can be derived, for instance, by reverse transcription from the mRNA encoded by the neukinase gene and lacks internal non-coding segments and transcription regulatory sequences present in the neukinase gene. An exemplary human neukinase cDNA is shown as SEQ ID NO:4.

As used herein, "vector" refers to discrete elements that are used to introduce heterologous DNA into cells for either expression or replication thereof. Selection and use of such vehicles are well known within the skill of the artisan. An expression vector includes vectors capable of expressing DNA that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "transgenic animals" refers to non-human animals, preferably mammals, more preferably rodents such as rats or mice, in which one or more of the cells includes a transgene. Other transgenic animals include primates, sheep, rabbits, hamsters, dogs, cows, goats, chickens, amphibians, etc. A "transgene" is exogenous DNA that is integrated into the genome of a cell from which a transgenic animal develops, and which remains in the genome of the mature animal.

As used herein, a "homologous recombinant animal" refers to a non-human animal, preferably a mammal, more preferably a rodent such as a rat or mouse, in which the endogenous neukinase gene has been altered by an exogenous DNA molecule that recombines homologously with endogenous neukinase in a (e.g., embryonic) cell prior to development of the animal. Other homologous recombinant animals include rabbits, hamsters and sheep. Host cells with exogenous neukinase can be used to produce non-human transgenic animals, such as fertilized oocytes or embryonic stem cells into which neukinase-encoding sequences have been introduced. Such host cells can then be used to create non-human transgenic animals or homologous recombinant animals.

As used herein, the term "biological sample" includes tissues, cells and biological fluids isolated from a subject, as well as tissues, cells and fluids present within a subject.

As used herein, the term "pharmaceutically acceptable" means approved by a regulatory agency of the Federal or a state government, or listed in the U.S. Pharmacopeia or other generally recognized pharmacopeia for use in animals, and more particularly in humans.

As used herein, the term "carrier" refers to a diluent, adjuvant, excipient, or vehicle with which a therapeutic of the invention is administered. Such pharmaceutical carriers can be sterile liquids, such as water and oils, including those of petroleum, animal, vegetable or synthetic origin, such as peanut oil, soybean oil, mineral oil, sesame oil and the like.

As used herein, "ejection fraction" or "EF" means the portion of blood that is pumped out of a filled left ventricle (LV) as the result of a heartbeat. It may be defined by the following formula: (LV diastolic volume–LV systolic volume)/LV diastolic volume.

As used herein, "fractional shortening" or "FS" means a ratio of the change in the diameter of the left ventricle between the contracted and relaxed states. It may be defined by the following formula: (LV end diastolic diameter–LV end systolic diameter)/LV end diastolic diameter.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, or idiopathic forms. Chronic cardiac hypertrophy is a significantly diseased state which is a precursor to congestive heart failure and cardiac arrest.

As used herein, "myocardial infarction" refers to a blockade of a coronary artery or blood flow interruption leading to focal necrosis of part of the myocardium caused by severe and persistent ischemia.

As used herein, "ventricular muscle cell hypertrophy" is synonymous with cardiac hypertrophy and refers to a condition characterized by an increase in the size of individual ventricular muscle cells, the increase in cell size being sufficient to result in a clinical diagnosis of the patient or sufficient as to allow the cells to be determined as larger (e.g., 2-fold or more larger than non-hypertrophic cells). It may be accompanied by accumulation of contractile proteins within the individual cardiac cells and activation of embryonic gene expression. In vitro and in vivo methods for determining the presence of ventricular muscle cell hypertrophy are known to those skilled in the art. In vitro assays for ventricular muscle cell hypertrophy include those methods described herein, e.g., increased cell size and increased expression of atrial natriuretic factor (ANF). Changes in cell size are used in a scoring system to determine the extent of hypertrophy. These changes can be viewed with an inverted phase microscope, and the degree of hypertrophy scored with an arbitrary scale of 7 to 0, with 7 being fully hypertrophied cells, and 3 being non-stimulated cells. The 3 and 7 states may be seen in Simpson et al., *Circulation Res.* 51: 787-801 (1982), FIG. 2, A and B, respectively. The correlation between hypertrophy score and cell surface area ($\mu m^2$) has been determined to be linear (correlation coefficient=0.99). In phenylephrine-induced hypertrophy, non-exposed (normal) cells have a hypertrophy score of 3 and a surface area/cell of 581 $\mu m^2$, and fully hypertrophied cells have a hypertrophy score of 7 and a surface area/cell of 1811 $\mu m^2$, or approximately 200% of normal. Cells with a hypertrophy score of 4 have a surface area/cell of 771 $\mu m^2$, or approximately 30% greater size than non-exposed cells; cells with a hypertrophy score of 5 have a surface area/cell of 1109 $\mu m^2$, or approximately 90% greater size than non-exposed cells; and cells with a hypertrophy score of 6 have a surface area/cell of 1366 $\mu m^2$, or approximately 135% greater size than non-exposed cells. The presence of ventricular muscle cell hypertrophy preferably includes cells exhibiting an increased size of about 15% (hypertrophy score 3.5) or more. Inducers of hypertrophy vary in their ability to induce a maximal hypertrophic response as scored by the above-described assay. For example, the maximal increase in cell size induced by endothelin is approximately a hypertrophy score of 5.

As used herein, "suppression" of ventricular muscle cell hypertrophy means a reduction in one of the parameters indicating hypertrophy relative to the hypertrophic condition, or a prevention of an increase in one of the parameters indicating hypertrophy relative to the normal condition. For example, suppression of ventricular muscle cell hypertrophy can be measured as a reduction in cell size relative to the hypertrophic condition. Suppression of ventricular muscle cell hypertrophy means a decrease of cell size of 10% or greater relative to that observed in the hypertrophic condition. More preferably, suppression of hypertrophy means a decrease in cell size of 30% or greater; most preferably, suppression of hypertrophy means a decrease of cell size of 50% or more. Relative to the hypertrophy score assay when phenylephrine is used as the inducing agent, these decreases would correlate with hypertrophy scores of about 6.5 or less, 5.0-5.5, and 4.0-5.0, respectively. When a different agent is used as the inducing agent, suppression is measured relative to the maximum cell size (or hypertrophic score) measured in the presence of that inducer.

Prevention of ventricular muscle cell hypertrophy can be determined by preventing an increase in cell size relative to normal cells, in the presence of a concentration of inducer sufficient to fully induce hypertrophy. For example, prevention of hypertrophy means a cell size increase less than 200% greater than non-induced cells in the presence of maximally-stimulating concentration of inducer. More preferably, prevention of hypertrophy means a cell size increase less than 135% greater than non-induced cells; and most preferably, prevention of hypertrophy means a cell size increase less than 90% greater than non-induced cells. Relative to the hypertrophy score assay when phenylephrine is used as the inducing agent, prevention of hypertrophy in the presence of a maximally-stimulating concentration of phenylephrine means a hypertrophic score of about 6.0-6.5, 5.0-5.5, and 4.0-4.5, respectively.

The in vivo determination of hypertrophy includes measurement of cardiovascular parameters such as blood pressure, heart rate, systemic vascular resistance, contractility, force of heart beat, concentric or dilated hypertrophy, left ventricular systolic pressure, left ventricular mean pressure, left ventricular end-diastolic pressure, cardiac output, stroke index, histological parameters, and ventricular size and wall thickness. Animal models available for determination of development and suppression of ventricular muscle cell hypertrophy in vivo include the pressure-overload mouse model, RV murine dysfunctional model, transgenic mouse model, and post-myocardial infarction rat model. Medical methods for assessing the presence, development, and suppression of ventricular muscle cell hypertrophy in human patients are known, and include, for example, measurements of diastolic and systolic parameters, estimates of ventricular mass, and pulmonary vein flows.

As used herein, an "effective amount" of an active agent for treating a particular disease is an amount that is sufficient to ameliorate, or in some manner reduce the symptoms associated with the disease. The amount may cure the disease but, typically, is administered in order to ameliorate the symptoms of the disease.

As used herein, "active agent" means any substance intended for the diagnosis, cure, mitigation, treatment, or prevention of disease in humans and other animals, or to otherwise enhance physical and mental well being.

The terms "treatment," "treating," and the like are used herein to generally mean obtaining a desired pharmacological and/or physiological effect in a subject actively suffering from a condition. The effect may completely or partially treat a disease or symptom thereof and thus may be therapeutic in terms of a partial or complete cure for a disease and/or adverse effect attributable to the disease. "Treatment" as used herein covers any treatment of a disease in a mammal, particularly a human, and includes inhibiting the disease, i.e., arresting its development; or relieving the disease, i.e., causing regression of the disease. In one example, treatment refers to treating patients with, or at risk for, development of heart disease and related conditions, e.g., heart failure. More specifically, "treatment" is intended to mean providing a therapeutically detectable and beneficial effect on a patient suffering from heart disease.

The terms "prevent," "preventing," and the like are used herein to generally refer to preventing a disease from occurring in a subject which may be predisposed to the disease but has not yet been diagnosed as suffering from the disease. Thus, "prevent" can refer to prophylactic or preventative measures, wherein the object is to prevent or slow down (lessen) cardiac hypertrophy.

5.2 Polypeptides of the Invention

The present invention provides newly identified and isolated polypeptides referred to in the present application as rat neukinase and human neukinase, respectively. In some embodiments, the polypeptides are native sequence rat and native sequence human neukinase polypeptides. In some embodiments, the polypeptides comprise substantially the same amino acid sequences as found in the native neukinase sequences. In certain embodiments, the invention provides amino acid sequences of functional fragments and variants of neukinase that comprise an antigenic determinant (i.e., a portion of a polypeptide that can be recognized by an antibody) or which are otherwise functionally active, as well as nucleic acids encoding the foregoing. Neukinase functional activity encompasses one or more known functional activities associated with a full-length (wild-type) neukinase polypeptide, e.g., myosin light chain kinase biological activity; antigenicity (the ability to be bound by an antibody to a protein consisting of the amino acid sequence of SEQ ID NOS: 1 or 2); immunogenicity (the ability to induce the production of an antibody that binds SEQ ID NOS: 1 or 2), and so forth.

In some embodiments, the polypeptides comprise the amino acid sequences having functionally inconsequential amino acid substitutions, and thus have amino acid sequences which differ from that of the native neukinase sequence. Substitutions can be introduced by mutation into neukinase-encoding nucleic acid sequences that result in alterations in the amino acid sequences of the encoded neukinase but do not alter neukinase function. For example, nucleotide substitutions leading to amino acid substitutions at "non-essential" amino acid residues can be made in neukinase encoding sequences. A "non-essential" amino acid residue is a residue that can be altered from the wild-type sequence of neukinase without altering myosin light chain kinase biological activity, whereas an "essential" amino acid residue is required for such biological activity. For example, amino acid residues that are conserved among the neukinase polypeptides of the invention are predicted to be particularly unsuitable for alteration. Amino acids for which conservative substitutions can be made are well known in the art.

Useful conservative substitutions are shown in Table 1, "Preferred Substitutions." Conservative substitutions whereby an amino acid of one class is replaced with another amino acid of the same type fall within the scope of the subject invention so long as the substitution does not materially alter the biological activity of the compound. If such substitutions result in a change in biological activity, then more substantial changes, indicated in Table 2 as exemplary are introduced and the products screened for neukinase polypeptide biological activity.

TABLE 1

Preferred Substitutions

| | | |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that effect: (1) the structure of the polypeptide backbone, such as a β-sheet or α-helical conformation; (2) the charge; (3) hydrophobicity; or (4) the bulk of the side chain of the target site, can modify neukinase polypeptide function or immunological identity. Residues are divided into groups based on common side-chain properties as denoted in Table 2. Non-conservative substitutions entail exchanging a member of one of these classes for another class. Substitutions may be introduced into conservative substitution sites or more preferably into non-conserved sites.

TABLE 2

Amino acid classes

| Class | Amino Acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (see Carter, *Biochem. J.* 237:1-7 (1986); Zoller and Smith, *Methods Enzymol.* 154: 329-50 (1987)), cassette mutagenesis, restriction selection mutagenesis (Wells et al., *Gene* 34:315-323 (1985)) or other known techniques can be performed on cloned neukinase-encoding DNA to produce neukinase variant DNA (Ausubel et al., *Current Protocols In Molecular Biology*, John Wiley and Sons, New York (current edition); Sambrook et al., *Molecular Cloning, A Laboratory Manual*, 3d. ed., Cold Spring Harbor Laboratory Press, Cold Spring Harbor, N.Y. (2001).

In certain embodiments, neukinase used in the present invention includes neukinase mutants or derivatives having an amino acid substitution with a non-classical amino acid or chemical amino acid analog. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

In one embodiment, the present invention includes an isolated polypeptide comprising an amino acid sequence having at least 70% identity to SEQ ID NO:1. In some embodiments, the polypeptide comprises an amino acid sequence having at least 75%, 80%, 85%, 90%, or 95% identity to SEQ ID NO:1. In a particular embodiment, the isolated polypeptide comprises the amino acid sequence of SEQ ID NO:1.

The present invention also includes an isolated polypeptide comprising an amino acid sequence having at least 70% identity to SEQ ID NO:2. In some embodiments, the polypeptide comprises an amino acid sequence having at least 75%, 80%, 85%, 90%, or 95% identity to SEQ ID NO:2. In a particular embodiment, the isolated polypeptide comprises the amino acid sequence of SEQ ID NO:2.

The present invention also includes an isolated polypeptide comprising an amino acid sequence having at least 70% identity to SEQ ID NO:25. In some embodiments, the polypeptide comprises an amino acid sequence having at least 75%, 80%, 85%, 90%, or 95% identity to SEQ ID NO:25. In a particular embodiment, the isolated polypeptide comprises the amino acid sequence of SEQ ID NO:25.

Percent identity in this context means the percentage of amino acid residues in the candidate sequence that are identical (i.e., the amino acid residues at a given position in the alignment are the same residue) or similar (i.e., the amino acid substitution at a given position in the alignment is a conservative substitution, as discussed above), to the corresponding amino acid residue in the peptide after aligning the sequences and introducing gaps, if necessary, to achieve the maximum percent sequence homology. In certain embodiments, a neukinase homologue is characterized by its percent sequence identity or percent sequence similarity with the naturally occurring neukinase sequence. Sequence homology, including percentages of sequence identity and similarity, are determined using sequence alignment techniques well-known in the art, preferably computer algorithms designed for this purpose, using the default parameters of said computer algorithms or the software packages containing them.

Non-limiting examples of computer algorithms and software packages incorporating such algorithms include the following. The BLAST family of programs exemplify a preferred, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and XBLAST), Altschul et al., 1997, *Nucleic Acids Res.* 25:3389-3402 (describing Gapped BLAST, and PSI-Blast). Another preferred example is the algorithm of Myers and Miller (1988 *CABIOS* 4:11-17) which is incorporated into the ALIGN program (version 2.0) and is available as part of the GCG sequence alignment software package. Also preferred is the FASTA program (Pearson W. R. and Lipman D. J., *Proc. Nat. Acad. Sci. USA*, 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

Examples of homologues may be the ortholog proteins of other species including animals, plants, yeast, bacteria, and the like. Homologues may also be selected by, e.g., mutagenesis in a native protein. For example, homologues may be identified by site-specific mutagenesis in combination with assays for detecting protein-protein interactions. Additional methods, e.g., protein affinity chromatography, affinity blotting, in vitro binding assays, and the like, will be apparent to skilled artisans apprised of the present invention.

For the purpose of comparing two different nucleic acid or polypeptide sequences, one sequence (test sequence) may be described to be a specific "percent identical to" another sequence (reference sequence) in the present disclosure. In this respect, when the length of the test sequence is less than 90% of the length of the reference sequence, the percentage identity is determined by the algorithm of Myers and Miller, *Bull. Math. Biol.*, 51:5-37 (1989) and Myers and Miller, *Comput. Appl. Biosci.*, 4(1):11-17 (1988). Specifically, the identity is determined by the ALIGN program. The default parameters can be used.

Where the length of the test sequence is at least 90% of the length of the reference sequence, the percentage identity is determined by the algorithm of Karlin and Altschul, *Proc. Natl. Acad. Sci. USA*, 90:5873-77 (1993), which is incorporated into various BLAST programs. Specifically, the percentage identity is determined by the "BLAST 2 Sequences" tool. See Tatusova and Madden, *FEMS Microbiol. Lett.*, 174(2):247-250 (1999). For pairwise DNA-DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

In certain embodiments, the isolated polypeptides of the present invention are capable of phosphorylating the myosin light chain of cardiac myosin. In certain embodiments, the isolated polypeptides of the present invention are capable of phosphorylating a functional fragment or variant of myosin light chain of cardiac myosin. In certain embodiments, the isolated polypeptides are capable of phosphorylating the myosin light chain, or functional fragments or variants of myosin light chain, of cardiac myosin of a mammal. In certain embodiments, the mammal is a rat, mouse or human. In some embodiments, the isolated polypeptides are capable of phosphorylating the myosin light chain, or functional fragments or variants of myosin light chain, of rat cardiac myosin. In some embodiments, the isolated polypeptides are capable of phosphorylating the myosin light chain, or functional fragments or variants of myosin light chain, of mouse cardiac myosin. In particular embodiments, the isolated polypeptides are capable of phosphorylating the myosin light chain, or functional fragments or variants of myosin light chain, of human cardiac myosin.

In some embodiments, the isolated polypeptides of the present invention are capable of binding to, and can be activated by, $Ca^{2+}$/calmodulin. Although not intending to be bound by any particular theory of operation, it is believed that activation of myosin light chain kinases involves the binding of $Ca^{2+}$/calmodulin to a calmodulin-binding sequence in a conserved regulatory segment of the polypeptide, which also contains an autoinhibitory sequence. Binding of $Ca^{2+}$/calmodulin removes the autoinhibitory sequence from the catalytic core of the polypeptide, wherein the active site is exposed for protein substrate binding and phosphorylation. Accordingly, in certain aspects, the present invention provides isolated polypeptides having the above properties.

5.3 Nucleic Acids of the Invention

In another aspect, the present invention provides newly identified and isolated nucleotide sequences encoding rat neukinase and human neukinase respectively. In particular, nucleic acids encoding native sequence rat neukinase and native sequence human neukinase polypeptides have been identified and isolated.

The neukinase-encoding or related sequences provided by the instant invention include those nucleotide sequences encoding substantially the same amino acid sequences as found in native neukinase, as well as those encoded amino acid sequences having functionally inconsequential amino acid substitutions, and thus have amino acid sequences which differ from that of the native sequence. Examples include the substitution of one basic residue for another (i.e. Arg for Lys), the substitution of one hydrophobic residue for another (i.e. Leu for Ile), or the substitution of one aromatic residue for another (i.e. Phe for Tyr, etc.).

The invention further relates to fragments of neukinase. Nucleic acids encoding such fragments are thus also within the scope of the invention. The neukinase gene and neukinase-encoding nucleic acid sequences of the invention include human and related genes (homologues) in other species. In some embodiments, the neukinase gene and neukinase-encoding nucleic acid sequences are from vertebrates, or more particularly, mammals. In some embodiments, the neukinase gene and neukinase-encoding nucleic acid sequences are of rat origin. In a preferred embodiment of the invention, the neukinase gene and neukinase-encoding nucleic acid sequences are of human origin. In one aspect, the invention provides an isolated nucleic acid encoding a polypeptide comprising an amino acid sequence having at least 70% identity to SEQ ID NO:1. In some embodiments, the nucleic acid encodes a polypeptide comprising an amino acid sequence having at least 75%, 80%, 85%, 90%, or 95% identity to SEQ ID NO:1. In a particular embodiment, the isolated nucleic acid encodes a polypeptide comprising the amino acid sequence of SEQ ID NO:1.

In another embodiment, the invention provides an isolated nucleic acid comprising a nucleic acid sequence having at least 70% identity to at least about 500 contiguous nucleotides selected from SEQ ID NO:3 or the complement thereof. In some embodiments, the nucleic acid comprises a nucleic acid sequence having at least 70% identity to at least about 500, 600, 700, 800, 900, 1000, 1100, 1200, 1500, 2000, or 2500 contiguous nucleotides selected from SEQ ID NO:3. In some embodiments, the nucleic acid comprises a nucleic acid sequence having at least 75% identity to at least about 500 contiguous nucleotides selected from SEQ ID NO:3. In some embodiments, the nucleic acid comprises a nucleic acid sequence having at least 75% identity to at least about 500, 600, 700, 800, 900, 1000, 1100, 1200, 1500, 2000, or 2500 contiguous nucleotides selected from SEQ ID NO:3. In some embodiments, the nucleic acid comprises a nucleic acid sequence having at least 80% identity to at least about 500 contiguous nucleotides selected from SEQ ID NO:3. In some embodiments, the nucleic acid comprises a nucleic acid sequence having at least 80% identity to at least about 500, 600, 700, 800, 900, 1000, 1100, 1200, 1500, 2000, or 2500 contiguous nucleotides selected from SEQ ID NO:3. In some embodiments, the nucleic acid comprises a nucleic acid sequence having at least 85% identity to at least about 500 contiguous nucleotides selected from SEQ ID NO:3. In some embodiments, the nucleic acid comprises a nucleic acid sequence having at least 85% identity to at least about 500, 600, 700, 800, 900, 1000, 1100, 1200, 1500, 2000, or 2500 contiguous nucleotides selected from SEQ ID NO:3. In some embodiments, the nucleic acid comprises a nucleic acid sequence having at least 90% identity to at least about 500 contiguous nucleotides selected from SEQ ID NO:3. In some embodiments, the nucleic acid comprises a nucleic acid sequence having at least 90% identity to at least about 500, 600, 700, 800, 900, 1000, 1100, 1200, 1500, 2000, or 2500 contiguous nucleotides selected from SEQ ID NO:3. In some embodiments, the nucleic acid comprises a nucleic acid sequence having at least 95% identity to at least about 500 contiguous nucleotides selected from SEQ ID NO:3. In some embodiments, the nucleic acid comprises a nucleic acid sequence having at least 95% identity to at least about 500, 600, 700, 800, 900, 1000, 1100, 1200, 1500, 2000, or 2500 contiguous nucleotides selected from SEQ ID NO:3. In certain embodiments, the isolated nucleic acid comprises at least about 500 nucleotides selected from the nucleic acid sequence of SEQ ID NO:3, or the complement thereof. In certain embodiments, the isolated nucleic acid comprises at least about 500, 600, 700, 800, 900, 1000, 1100, 1200, 1500, 2000, or 2500 nucleotides selected from the nucleic acid sequence of SEQ ID NO:3, or the complement thereof. In a particular embodiment, the isolated nucleic acid comprises the nucleic acid sequence of SEQ ID NO:3, or the complement thereof.

In another aspect, the invention provides an isolated nucleic acid encoding a polypeptide comprising an amino acid sequence having at least 70% identity to SEQ ID NO:2. In some embodiments, the nucleic acid encodes a polypeptide comprising an amino acid sequence having at least 75%, 80%, 85%, 90%, or 95% identity to SEQ ID NO:2. In a particular embodiment, the isolated nucleic acid encodes a polypeptide comprising the amino acid sequence of SEQ ID NO:2.

In another aspect, the invention provides an isolated nucleic acid encoding a polypeptide comprising an amino acid sequence having at least 70% identity to SEQ ID NO:25. In some embodiments, the nucleic acid encodes a polypeptide comprising an amino acid sequence having at least 75%, 80%, 85%, 90%, or 95% identity to SEQ ID NO:25. In a particular embodiment, the isolated nucleic acid encodes a polypeptide comprising the amino acid sequence of SEQ ID NO:25.

In another aspect, the invention provides an isolated nucleic acid comprising a nucleic acid sequence having at least 70% identity to at least about 500 contiguous nucleotides selected from SEQ ID NO:4 or the complement thereof. In some embodiments, the nucleic acid comprises a nucleic acid sequence having at least 70% identity to at least about 500, 600, 700, 800, 900, 1000, 1100, 1200, 1500, 2000, or 2500 contiguous nucleotides selected from SEQ ID NO:4. In some embodiments, the nucleic acid comprises a nucleic acid sequence having at least 75% identity to at least about 500 contiguous nucleotides selected from SEQ ID NO:4. In some embodiments, the nucleic acid comprises a nucleic acid sequence having at least 75% identity to at least about 500, 600, 700, 800, 900, 1000, 1100, 1200, 1500, 2000, or 2500 contiguous nucleotides selected from SEQ ID NO:4. In some embodiments, the nucleic acid comprises a nucleic acid sequence having at least 80% identity to at least about 500 contiguous nucleotides selected from SEQ ID NO:4. In some embodiments, the nucleic acid comprises a nucleic acid sequence having at least 80% identity to at least about 500, 600, 700, 800, 900, 1000, 1100, 1200, 1500, 2000, or 2500 contiguous nucleotides selected from SEQ ID NO:4. In some embodiments, the nucleic acid comprises a nucleic acid sequence having at least 85% identity to at least about 500 contiguous nucleotides selected from SEQ ID NO:4. In some embodiments, the nucleic acid comprises a nucleic acid sequence having at least 85% identity to at least about 500, 600, 700, 800, 900, 1000, 1100, 1200, 1500, 2000, or 2500 contiguous nucleotides selected from SEQ ID NO:4. In some embodiments, the nucleic acid comprises a nucleic acid sequence having at least 90% identity to at least about 500 contiguous nucleotides selected from SEQ ID NO:4. In some embodiments, the nucleic acid comprises a nucleic acid sequence having at least 90% identity to at least about 500, 600, 700, 800, 900, 1000, 1100, 1200, 1500, 2000, or 2500 contiguous nucleotides selected from SEQ ID NO:4. In some embodiments, the nucleic acid comprises a nucleic acid sequence having at least 95% identity to at least about 500 contiguous nucleotides selected from SEQ ID NO:4. In some embodiments, the nucleic acid comprises a nucleic acid sequence having at least 95% identity to at least about 500, 600, 700, 800, 900, 1000, 1100, 1200, 1500, 2000, or 2500 contiguous nucleotides selected from SEQ ID NO:4. In certain embodiments, the isolated nucleic acid comprises at least about 500 nucleotides selected from the nucleic acid sequence of SEQ ID NO:4, or the complement thereof. In certain embodiments, the isolated nucleic acid comprises at least about 500, 600, 700, 800, 900, 1000, 1100, 1200, 1500, 2000, or 2500 nucleotides selected from the nucleic acid sequence of SEQ ID NO:4, or the complement thereof. In a particular embodiment, the isolated nucleic acid comprises the nucleic acid sequence of SEQ ID NO:4, or the complement thereof.

The present invention also includes nucleic acids that hybridize to or are complementary to the foregoing sequences. In specific aspects, nucleic acids are provided which comprise a sequence complementary to at least 20, 30, 40, 50, 100, 200 nucleotides or the entire coding region of neukinase, or the reverse complement (antisense) of any of these sequences. In a specific embodiment, a nucleic acid which hybridizes to a neukinase nucleic acid sequence (e.g., having part or the whole of sequence SEQ ID NO:3 or SEQ ID NO:4, or the complements thereof), under conditions of low stringency is provided. In some embodiments, said nucleic acid corresponds to SEQ ID NO:7. In other embodiments, said nucleic acid corresponds to SEQ ID NO:8, or a portion thereof.

By way of example and not limitation, procedures using such conditions of low stringency are as follows (see also Shilo and Weinberg, 1981, *Proc. Natl. Acad. Sci. U.S.A.* 78:6789-6792). Filters containing DNA can be pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations can be carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe can be used. Filters can be incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution can then be replaced with fresh solution and incubated an additional 1.5 h at 60° C. Filters may be blotted dry and exposed for autoradiography. If necessary, filters may be washed for a third time at 65-68° C. and re-exposed to film. Other conditions of low stringency which may be used are well known in the art (e.g., as employed for cross-species hybridizations).

In another specific embodiment, a nucleic acid that hybridizes to a nucleic acid encoding neukinase, or its reverse complement, under conditions of high stringency is provided. By way of example and not limitation, procedures using such conditions of high stringency are as follows. Prehybridization of filters containing DNA may be carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters may be hybridized for 48 h at 65° C. in prehybridization mixture containing 100 µg/ml denatured salmon sperm DNA and 5-20×10$^6$ cpm of $^{32}$P-labeled probe. Washing of filters may be done at 37° C. for 1 h in a solution containing 2×SSC, 0.01% PVP, 0.01% Ficoll, and 0.01% BSA. This can be followed by a wash in 0.1×SSC at 50° C. for 45 minutes before autoradiography. Other conditions of high stringency that may be used are well known in the art.

5.3.1 Cloning of the Neukinase Gene or cDNA

The present invention further provides methods and compositions relating to the cloning of a gene or cDNA encoding neukinase. In one embodiment of the invention, expression cloning (a technique commonly known in the art), may be used to isolate a gene or cDNA encoding neukinase. An expression library may be constructed by any method known in the art. In one embodiment, mRNA (e.g., human) is isolated, and cDNA is made and ligated into an expression vector such that the cDNA is capable of being expressed by the host cell into which it is introduced. Various screening assays can then be used to select for the expressed neukinase product. In one embodiment, anti-neukinase antibodies can be used for selection.

In another embodiment of the invention, polymerase chain reaction (PCR) may be used to amplify desired nucleic acid sequences of the present invention from a genomic or cDNA library. Isolated oligonucleotide primers representing known neukinase-encoding sequences can be used as primers in PCR. In certain embodiments, the isolated oligonucleotide primer comprises at least 10 consecutive nucleotides of SEQ ID NO:3 or its complimentary strand. In certain embodiments, the isolated oligonucleotide primer comprises at least 10 consecutive nucleotides of SEQ ID NO:4 or its complimentary strand. In some embodiments, the isolated oligonucleotide primer comprises the nucleic acid sequence of SEQ ID NO:5. In some embodiments, the isolated oligonucleotide primer comprises the nucleic acid sequence of SEQ ID NO:6. In a preferred aspect, the oligonucleotide primers represent at least part of the conserved segments of strong homology between neukinase-encoding genes of different species. The synthetic oligonucleotides may be utilized as primers to amplify by PCR sequences from RNA or DNA, preferably a cDNA library, of potential interest. Alternatively, one can synthesize degenerate primers for use in the PCR reactions.

In the PCR reactions, the nucleic acid being amplified can include RNA or DNA, for example, mRNA, cDNA or genomic DNA from any eukaryotic species. PCR can be carried out, e.g., by use of a Perkin-Elmer Cetus thermal cycler and Taq polymerase. It is also possible to vary the stringency of hybridization conditions used in priming the PCR reactions, to allow for greater or lesser degrees of nucleotide sequence similarity between a known neukinase nucleotide sequence and a nucleic acid homologue being isolated. For cross-species hybridization, low stringency conditions are preferred. For same-species hybridization, moderately stringent conditions are preferred. After successful amplification of a segment of a neukinase homologue, that segment may be cloned, sequenced, and utilized as a probe to isolate a complete cDNA or genomic clone. This, in turn, will permit the determination of the gene's complete nucleotide sequence, the analysis of its expression, and the production of its protein product for functional analysis. In this fashion, additional nucleotide sequences encoding neukinase or neukinase homologues may be identified.

The above recited methods are not meant to limit the following general description of methods by which clones of genes encoding neukinase or homologues thereof may be obtained.

Any eukaryotic cell potentially can serve as the nucleic acid source for the molecular cloning of the neukinase gene, neukinase cDNA or a homologue thereof. The nucleic acid sequences encoding neukinase can be isolated from vertebrate, mammalian, human, porcine, bovine, feline, avian, equine, canine, as well as additional primate sources. The DNA may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual*, 3d. ed., Cold Spring Harbor Laboratory Press, Cold Spring Harbor, N.Y. (2001); Glover, D. M. (ed.), *DNA Cloning: A*

*Practical Approach,* 2d. ed., MRL Press, Ltd., Oxford, U.K. (1995). Clones derived from genomic DNA may contain regulatory and intron DNA regions in addition to coding regions; clones derived from cDNA will contain only exon sequences. Whatever the source, the gene may be cloned into a suitable vector for propagation of the gene.

In the cloning of the gene from genomic DNA, DNA fragments are generated, some of which will encode the desired gene. The DNA may be cleaved at specific sites using various restriction enzymes. Alternatively, one may use DNase in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if a neukinase gene (of any species) or its specific RNA is available and can be purified and labeled, the generated DNA fragments may be screened by nucleic acid hybridization to the labeled probe (Benton and Davis, *Science* 196:180 (1977); Grunstein and Hogness, *Proc. Natl. Acad. Sci. U.S.A.* 72:3961 (1975). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the gene may be detected by assays based on the physical, chemical, or immunological properties of its expressed product. For example, cDNA clones, or DNA clones that hybrid-select the proper mRNAs, can be selected that produce a protein having e.g., similar or identical electrophoretic migration, isoelectric focusing behavior, proteolytic digestion maps, substrate binding activity, or antigenic properties as known for a specific neukinase. If an antibody to a particular neukinase is available, that neukinase may be identified by binding of labeled antibody to the clone(s) putatively producing the neukinase in an ELISA (enzyme-linked immunosorbent assay)-type procedure.

A neukinase or homologue thereof can also be identified by mRNA selection by nucleic acid hybridization followed by in vitro translation. In this procedure, fragments are used to isolate complementary mRNAs by hybridization. Such DNA fragments may represent available, purified DNA of another species containing a gene encoding neukinase. Immunoprecipitation analysis or functional assays of the in vitro translation products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against a specific neukinase. A radiolabelled neukinase-encoding cDNA can be synthesized using the selected mRNA (from the adsorbed polysomes) as a template. The radiolabelled mRNA or cDNA may then be used as a probe to identify the neukinase-encoding DNA fragments from among other genomic DNA fragments.

Alternatives to isolating the neukinase genomic DNA include, but are not limited to, chemically synthesizing the gene sequence itself from a known sequence or making cDNA to the mRNA which encodes neukinase. For example RNA for the cloning of neukinase cDNA can be isolated from cells that express a neukinase gene. Other methods are possible and within the scope of the invention.

The identified and isolated neukinase or neukinase analog-encoding gene can then be inserted into an appropriate cloning vector. A large number of vector-host systems known in the art may be used. Possible cloning vectors include, but are not limited to, plasmids or modified viruses, but the vector system must be compatible with the host cell used. Such vectors include, but are not limited to bacteriophages such as lambda derivatives, or plasmids such as pBR322, pUC plasmid derivatives, or the pBluescript vector. (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini. These ligated linkers may comprise specific chemically synthesized oligonucleotides encoding restriction endonuclease recognition sequences. In an alternative method, the cleaved vector and neukinase-encoding gene or nucleic acid sequence may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shotgun" approach. Enrichment for the desired gene, for example, by size fractionization, can be done before insertion into the cloning vector.

To generate multiple copies of the isolated neukinase-encoding gene, cDNA, or synthesized DNA sequence, host cells, for example competent strains of *E. Coli*, may be transformed with recombinant DNA molecules incorporating said sequences according to any technique known in the art. Thus, the gene may be obtained in large quantities by growing transformants, isolating the recombinant DNA molecules from the transformants and, when necessary, retrieving the inserted gene from the isolated recombinant DNA.

5.3.2 Expression Vectors

In still another aspect, the invention provides expression vectors for expressing isolated neukinase-encoding cDNA sequences. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation of mRNA. Techniques for construction of expression vectors and expression of genes in cells comprising the expression vectors are well known in the art. See, e.g., Sambrook et al., 2001, *Molecular Cloning—A Laboratory Manual,* 3$^{rd}$ edition, Cold Spring Harbor Laboratory, Cold Spring Harbor, N.Y., and Ausubel et al., eds., Current Edition, *Current Protocols in Molecular Biology,* Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, an RSV promoter, a tetracycline-inducible CMV promoter (such as the human immediate-early CMV promoter), and a constitutive CMV promoter.

The expression vectors should contain expression and replication signals compatible with the cell in which the neukinase-encoding sequences are to be expressed. Expression vectors useful for expressing neukinase-encoding sequences include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells.

The expression vectors can be introduced into the cell for expression of the neukinase-encoding sequence by any method known to one of skill in the art without limitation. Such methods include, but are not limited to, e.g., direct uptake of the recombinant DNA molecule by a cell from solution; facilitated uptake through lipofection using, e.g., liposomes or immunoliposomes; particle-mediated transfection; etc. See, e.g., U.S. Pat. No. 5,272,065; Goeddel et al., *Methods in Enzymology*, vol. 185, Academic Press, Inc., CA (1990); Krieger, *Gene Transfer and Expression—A Laboratory Manual*, Stockton Press, New York (1990); Ausubel et al., *Current Protocols In Molecular Biology*, John Wiley and Sons, New York (current edition); Sambrook et al., *Molecular Cloning, A Laboratory Manual*, 3d. ed., Cold Spring Harbor Laboratory Press, Cold Spring Harbor, N.Y. (2001).

The expression vectors can also contain a purification moiety that simplifies isolation of the expressed protein. For example, a polyhistidine moiety of, e.g., six histidine residues, can be incorporated at the amino terminal end of the protein. The polyhistidine moiety allows convenient isolation of the protein in a single step by nickel-chelate chromatography. In certain embodiments, the purification moiety can be cleaved from the remainder of the delivery construct following purification. In other embodiments, the moiety does not interfere with the function of the functional domains of the expressed protein and thus need not be cleaved.

5.3.3 Cells

In yet another aspect, the invention provides a cell comprising an expression vector for expression of neukinase polypeptides of the invention, or portions thereof. The cell is preferably selected for its ability to express high concentrations of the neukinase polypeptide to facilitate subsequent purification of the polypeptide. In certain embodiments, the cell is a prokaryotic cell, for example, *E. coli*. In a preferred embodiment, the neukinase polypeptide is properly folded and comprises the appropriate disulfide linkages when expressed in *E. coli*.

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the delivery constructs. For example, Chinese hamster ovary (CHO) cells can be used to express the neukinase polypeptides of the invention. In some embodiments, the neukinase polypeptide is expressed in neonatal rat ventricular myocytes. In some embodiments, the neukinase polypeptide is expressed in H9c2(2-1) cells.

5.4 Antibodies

According to the invention, neukinase, or its fragments thereof, may be used as an immunogen to generate antibodies which immunospecifically bind neukinase polypeptides. Such antibodies include, but are not limited to, polyclonal, monoclonal, single chain monoclonal, recombinant, chimeric, humanized, mammalian, or human antibodies.

In some embodiments, antibodies to a non-human neukinase are produced. In certain embodiments, antibodies to rat neukinase are produced. In other embodiments, antibodies to human neukinase are produced. In another embodiment, antibodies are produced that specifically bind to a protein the amino acid sequence of which consists of SEQ ID NO:1. In another embodiment, antibodies are produced that specifically bind to a protein the amino acid sequence of which consists of SEQ ID NO:2. In another embodiment, antibodies are produced that specifically bind to a protein the amino acid sequence of which consists of SEQ ID NO:25. In another embodiment, antibodies to a fragment of non-human neukinase are produced. In another embodiment, antibodies to a fragment of rat neukinase are produced. In another embodiment, antibodies to a fragment of human neukinase are produced. In a specific embodiment, fragments of neukinase, human or non-human, identified as containing hydrophilic regions are used as immunogens for antibody production. In a specific embodiment, a hydrophilicity analysis can be used to identify hydrophilic regions of neukinase, which are potential epitopes, and thus can be used as immunogens.

For the production of antibody, various host animals can be immunized by injection with native neukinase, or a synthetic version, or a fragment thereof. In certain embodiments, the host animal is a mammal. In some embodiments, the mammal is a rabbit, mouse, rat, goat, cow or horse.

For the production of polyclonal antibodies to neukinase, various procedures known in the art may be used. In a particular embodiment, rabbit polyclonal antibodies to an epitope of neukinase encoded by a sequence of SEQ ID NO:3 or SEQ ID NO:4 or a subsequence thereof, can be obtained. Various adjuvants may be used to increase the immunological response, depending on the host species. Adjuvants that may be used according to the present invention include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, CpG-containing nucleic acids, and potentially useful human adjuvants such as BCG (bacille Calmette-Guerin) and *Corynebacterium parvum*.

For preparation of monoclonal antibodies directed toward a neukinase polypeptide, any technique that provides for the production of antibody molecules by continuous cell lines in culture may be used. For example, monoclonal antibodies may be prepared by the hybridoma technique originally developed by Kohler and Milstein, *Nature* 256:495-497 (1975), as well as the trioma technique, the human B-cell hybridoma technique (Kozbor et al., *Immunol. Today* 4:72 (1983)), or the EBV-hybridoma technique (Cole et al., in *Monoclonal Antibodies and Cancer Therapy*, Alan R. Liss, Inc., pp. 77-96 (1985)).

Techniques for the production of single chain antibodies, as described in U.S. Pat. No. 4,946,778, can also be adapted to produce single chain antibodies specific to neukinase. An additional embodiment of the invention utilizes the techniques described for the construction of Fab expression libraries (Huse et al., *Science* 246:1275-1281 (1988)) to allow rapid and easy identification of monoclonal Fab fragments with the desired specificity for neukinase. Antibody fragments that contain the idiotype of the molecule can be generated by known techniques. For example, such fragments include but are not limited to: the F(ab'), fragment which can be produced by pepsin digestion of the antibody molecule; the Fab' fragments which can be generated by reducing the disulfide bridges of the F(ab'), fragment, the Fab fragments which can be generated by treating the antibody molecule with papain and a reducing agent, and Fv fragments.

Techniques developed for the production of "chimeric" antibodies (Morrison et al., *Proc. Natl. Acad. Sci. U.S.A.* 81:6851-6855 (1984); Neuberger et al., *Nature* 312:604-608 (1984); Takeda et al., *Nature* 314:452-454 (1985)) can also be used. For example, nucleic acid sequences encoding a mouse antibody molecule specific to neukinase are spliced to nucleic acid sequences encoding a human antibody molecule.

In addition, techniques have been developed for the production of humanized antibodies, and such humanized antibodies to neukinase are within the scope of the present invention. See, e.g., Queen, U.S. Pat. No. 5,585,089 and Winter, U.S. Pat. No. 5,225,539. An immunoglobulin light or heavy chain variable region consists of a "framework" region interrupted by three hypervariable regions, referred to as complementarity determining regions (CDRs). The extent of the framework region and CDRs have been precisely defined. *See, Sequences of Proteins of Immunological Interest*, Kabat, E. et al., U.S. Department of Health and Human Services (1983). Briefly, humanized antibodies are antibody molecules from non-human species having one or more CDRs from the non-human species and a framework region from a human immunoglobulin molecule.

Human antibodies may be used and can be obtained by using human hybridomas (Cote et al., *Proc. Natl. Acad. Sci. U.S.A.*, 80:2026-2030 (1983)) or by transforming human B cells with EBV virus in vitro (Cole et al., in *Monoclonal Antibodies and Cancer Therapy*, Alan R. Liss, pp. 77-96 (1985)).

In the production of antibodies, screening for the desired antibody can be accomplished by techniques known in the art, e.g. ELISA (enzyme-linked immunosorbent assay), RIA (radioimmunoassay) or RIBA (recombinant immunoblot assay). For example, to select antibodies which recognize a specific domain of neukinase, one may assay generated hybridomas for a product which binds to a neukinase fragment containing such domain. For selection of an antibody that specifically binds a first neukinase homologue but which does not specifically bind a second, different neukinase homologue, one can select on the basis of positive binding to the first neukinase homologue and a lack of binding to the second neukinase homologue.

Antibodies specific to a domain of neukinase or a homologue thereof are also provided. The foregoing antibodies can be used in methods known in the art relating to the localization and activity of the neukinase of the invention, e.g., for imaging these proteins, measuring levels thereof in appropriate physiological samples, in diagnostic methods, etc.

5.5 Transgenic Neukinase Animals

Transgenic animals are useful for studying the function and/or activity of neukinase and for identifying and/or evaluating modulators of neukinase activity. Transgenes direct the expression of an encoded gene product in one or more cell types or tissues of the transgenic animal. In some embodiments, transgenes prevent the expression of a naturally encoded gene product in one or more cell types or tissues (a "knockout" transgenic animal). In some embodiments, transgenes serve as a marker or indicator of an integration, chromosomal location, or region of recombination (e.g., cre/loxP mice).

A transgenic animal can be created by introducing a nucleic acid of the invention into the male pronuclei of a fertilized oocyte (e.g., by microinjection, retroviral infection) and allowing the oocyte to develop in a pseudopregnant female foster animal (PFFA). The neukinase sequences can be introduced as a transgene into the genome of a non-human animal. In some embodiments, the neukinase sequence is the rat neukinase sequence (SEQ ID NO:3). In some embodiments, the neukinase sequence is the human neukinase sequence (SEQ ID NO:4). In other embodiments, a homologue of neukinase can be used as a transgene. Intronic sequences and polyadenylation signals can also be included in the transgene to increase transgene expression. Tissue-specific regulatory sequences can be operably-linked to the neukinase transgene to direct expression of neukinase to particular cells. Methods for generating transgenic animals via embryo manipulation and microinjection, particularly animals such as mice, have become conventional in the art, e.g., Evans et al., U.S. Pat. No. 4,870,009 (1994); Leder and Stewart, U.S. Pat. No. 4,736,866, 1988; Wagner and Hoppe, U.S. Pat. No. 4,873,191 (1989). Other non-mice transgenic animals may be made by similar methods. A transgenic founder animal, which can be used to breed additional transgenic animals, can be identified based upon the presence of the transgene in its genome and/or expression of the transgene mRNA in tissues or cells of the animal. Transgenic neukinase animals can be bred to other transgenic animals carrying other transgenes.

To create a homologous recombinant animal, a vector containing at least a portion of neukinase into which a deletion, addition or substitution may be introduced to thereby alter, e.g., functionally disrupt neukinase expression. In some embodiments, the vector may contain a neomycin cassette inserted in reverse orientation relative to neukinase transcription to functionally disrupt neukinase. Neukinase can be a human gene (SEQ ID NO:10), or other neukinase homologue. In one approach, a knockout vector functionally disrupts the endogenous neukinase gene upon homologous recombination, and thus a non-functional neukinase protein, if any, is expressed.

Alternatively, the vector can be designed such that, upon homologous recombination, the endogenous neukinase is mutated or otherwise altered but still encodes functional protein (e.g., the upstream regulatory region can be altered to thereby alter the expression of endogenous neukinase). In this type of homologous recombination vector, the altered portion of the neukinase sequence is flanked at its 5'- and 3'-termini by additional nucleic acid sequence of neukinase to allow for homologous recombination to occur between the exogenous neukinase sequence carried by the vector and an endogenous neukinase sequence in an embryonic stem cell. The additional flanking neukinase sequence is sufficient to engender homologous recombination with endogenous neukinase. Typically, several kilobases of flanking DNA (both at the 5'- and 3'-termini) are included in the vector (see Thomas and Capecchi, *Cell* 51:503-512 (1987)).

The vector is then introduced into an embryonic stem cell line (e.g., by electroporation), and cells in which the introduced neukinase sequence has homologously-recombined with the endogenous neukinase sequence are selected (Li et al., *Cell* 69:915-926 (1992)).

Selected cells are then injected into a blastocyst of an animal (e.g., a mouse) to form aggregation chimeras (see Bradley, *Teratocarcinomas and Embryonic Stem Cells. A Practical Approach*, Oxford University Press, Inc., Oxford (1987)). A chimeric embryo can then be implanted into a suitable PFFA, wherein the embryo is brought to term.

Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described (Berns et al., WO 93/04169, 1993; Kucherlapati et al., WO 91/01140, 1991; Le Mouellic and Brullet, WO 90/11354, 1990).

Alternatively, transgenic animals that contain selected systems that allow for regulated expression of the transgene can be produced. An example of such a system is the cre/loxP recombinase system of bacteriophage P1 (Lakso et al., *Proc. Natl. Acad. Sci. USA* 89:6232-6236 (1992)). Another recombinase system is the FLP recombinase system of *Saccharomyces cerevisiae* (O'Gorman et al., *Science* 251:1351-1355 (1991)). If a cre/loxP recombinase system is used to regulate expression of the transgene, animals containing transgenes encoding both the Cre recombinase and a selected protein are required. Such animals can be produced as "double" transgenic animals, by mating an animal containing a transgene encoding a selected protein to another containing a transgene encoding a recombinase.

Clones of transgenic animals can also be produced (Wilmut et al., *Nature* 385:810-813 (1997)). In brief, a cell from a transgenic animal can be isolated and induced to exit the growth cycle and enter Go phase. The quiescent cell can then be fused to an enucleated oocyte from an animal of the same species from which the quiescent cell is isolated. The reconstructed oocyte is then cultured to develop to a morula or blastocyte and then transferred to a PFFA. The offspring borne of this female foster animal will be a clone of the "parent" transgenic animal.

5.6 Methods of Screening for Modulators of Neukinase Activity

The present invention also provides methods of identifying a compound that modulates the activity of neukinase in a cell or tissue of interest. A compound may modulate neukinase activity by affecting, for example: (1) the number of copies of the neukinase gene in the cell (amplifiers and deamplifiers); (2) increasing or decreasing transcription of the neukinase gene (transcription up-regulators and down-regulators); (3) by increasing or decreasing the translation of the neukinase mRNA into protein (translation up regulators and down regulators); or (4) by increasing or decreasing the activity of the neukinase protein (agonists and antagonists). To identify compounds that affect neukinase at the DNA, RNA, and protein levels, cells or organisms are contacted with a candidate compound and the corresponding change in neukinase DNA, RNA or protein may be assessed. For DNA amplifiers or deamplifiers, the amount of neukinase DNA may be measured. For those compounds that are transcription up-regulators and down-regulators, the amount of neukinase mRNA may be measured. Alternatively, the neukinase promoter sequence may be operably linked to a reporter gene, and potential transcriptional modulators of neukinase may be assayed by measuring reporter gene activity in the presence and absence of the compound. For translational up- and down-regulators, the amount of neukinase polypeptide may be measured. Alternatively, changes in neukinase biological activity, as measured by the techniques described below, may be an indirect indicator of the ability of a compound to modulate neukinase translation.

Neukinase activity of the methods described herein encompasses the biological activity of neukinase, which includes, but is not limited to, phosphorylation of cardiac myosin light chain and/or functional fragments or variants of myosin light chain, calmodulin binding, and autoinhibition. Methods for examining cell-based phosphorylation events are commonly known in the art, and may be utilized to examine changes in myosin light chain phosphorylation following contact with a putative modulator of neukinase biological activity.

In one embodiment, the cell or tissue useful for the methods described herein expresses a neukinase polypeptide from an endogenous copy of the neukinase gene. In another embodiment, the cell or tissue expresses a neukinase polypeptide following transient or stable transformation with a nucleic acid encoding a neukinase polypeptide of the present invention. Any mammalian cell known by one of skill in the art to be useful for expressing a recombinant polypeptide, without limitation, can be used to express a neukinase polypeptide useful for the methods described herein.

In one embodiment, the method of identifying a compound that modulates the activity of neukinase comprises determining a first level of neukinase activity in a cell or tissue that expresses a neukinase polypeptide, contacting said cell or tissue with a test compound, then determining a second level of neukinase activity in said cell or tissue. A difference in the first level and second level of neukinase activity is indicative of the ability of the test compound to modulate neukinase activity. In one embodiment, a compound may have agonistic activity if the second level of neukinase activity is greater than the first level of neukinase activity. In certain embodiments, agonistic activity comprises at least about a 2, 4, 6, 8, 10, or greater fold increase in the second level of neukinase activity compared to the first level of neukinase activity. In another embodiment, a compound may have antagonistic activity if the second level of neukinase activity is less than the first level of neukinase activity. In certain embodiments, antagonistic activity comprises at least about a 2, 4, 6, 8, 10, or greater fold decrease in the second level of neukinase activity compared to the first level of neukinase activity.

In another embodiment, the invention provides a method of identifying a compound that modulates the activity of neukinase in a cell or tissue expressing a neukinase polypeptide, comprising contacting said cell or tissue with a test compound and determining a level of neukinase in said cell or tissue. The difference in this level and a standard or baseline level of neukinase activity in a comparable cell or tissue, e.g., a control cell or tissue not contacted with the test compound, is indicative of the ability of said test compound to modulate neukinase activity. In one embodiment, a compound may have agonistic activity if the level of neukinase activity in the cell or tissue contacted with said compound is greater than the level of neukinase activity in the control cell or tissue. In certain embodiments, agonistic activity comprises at least about a 2-, 4-, 6-, 8-, 10-, or greater fold increase in the level of neukinase activity of a cell or tissue contacted with the test compound compared to the level of neukinase activity in the control cell or tissue. In another embodiment, a compound may have antagonistic activity if the level of neukinase activity in the cell or tissue contacted with said compound is less than the level of neukinase activity in the control cell or tissue. In certain embodiments, antagonistic activity comprises at least about a 2-, 4-, 6-, 8-, 10-, or greater fold decrease in the level of neukinase activity of a cell or tissue contacted with the test compound compared to the level of neukinase activity in the control cell or tissue.

The present invention also provides methods of identifying a compound that modulates the activity of neukinase in a transgenic non-human animal which expresses a neukinase polypeptide, comprising administering the compound to said animal and assessing the animal for an alteration in cardiac function affected by the compound. Cardiac function may be assessed through the measurement of interventricular septum size, left ventricle end diastolic dimension (LVEDD), posterior wall thickness, left ventricle end systolic dimension (LVESD), ejection fraction (EF), fractional shortening (FS), and cardiac cycle. In one embodiment, a compound may have agonistic activity if the LVEDD value following administration of the compound is reduced by at least about 2%, 5%, 10%, 15%, 20%, or greater. In another embodiment, a compound may have agonistic activity if the LVESD value following administration of the compound is reduced by at least about 2%, 5%, 10%, 15%, 20%, or greater. In another embodiment, a compound may have agonistic activity if the EF value of the left ventricle is enhanced by at least about 10%, 20%, 30%, 40%, 50%, 60% or greater. In another embodiment, a compound may have agonistic activity if the FS value of the left ventricle is enhanced by at least about 10%, 20%, 30%, 40%, 50%, 60% or greater.

The present invention also provides methods of identifying compounds that specifically bind to neukinase nucleic acids or polypeptides and thus have potential use as agonists or antagonists of neukinase. In certain embodiments, such compounds may affect cardiac hypertrophy, ventricular muscle cell hypertrophy, etc. In a preferred embodiment, assays are performed to screen for compounds having potential utility as heart failure therapies or lead compounds for drug development. The invention thus provides assays to detect compounds that specifically bind to neukinase nucleic acids or polypeptides. For example, recombinant cells expressing neukinase nucleic acids can be used to recombinantly produce neukinase polypeptides for use in these assays, e.g., to screen for compounds that bind to neukinase polypeptides. Said compounds (e.g., putative binding partners of neukinase) are contacted with a neukinase polypeptide or a fragment thereof under conditions conducive to binding, and compounds that specifically bind to neukinase are identified. Similar methods can be used to screen for compounds that bind to neukinase nucleic acids. Methods that can be used to carry out the foregoing are commonly known in the art.

In some embodiments, cell free assays utilizing a purified neukinase polypeptide may be performed to identify compounds which modulate (1) the phosphorylation of cardiac myosin light chain and/or functional fragments or variants thereof, (2) the autoinhibitory activity of neukinase in the absence of $Ca^{2+}$/calmodulin, and/or (3) neukinase binding of, and activation by, calmodulin. Myosin light chain kinase assays are well known in the art, and are described, for example, by Polak et al., *J. Neurosci.*, 11:534-54 (1991), Ausubel et al., *Current Protocols In Molecular Biology*, John Wiley and Sons, New York (current edition), and U.S. Pat. No. 5,906,810, the contents of which are hereby incorporated by reference in their entirety. Putative modulators of neukinase biological activity may be identified by assaying neukinase kinase activity in the presence of varying concentrations of the compound and examining the extent of phosphate incorporation into a suitable substrate. In some embodiments, the substrate is myosin light chain. In some embodiments, the substrate is a functional fragment of myosin light chain. In some embodiments, the substrate is a variant of myosin light chain.

In certain embodiments, modulation of neukinase activity may be measured by calmodulin activity assays, as described in U.S. Pat. No. 5,840,697, Sharma et al., *Adv. Cyclic Nucleotide Res.*, 10:187-89 (1979), and Wallace et al., *Methods Enzymol.*, 102:39-47 (1983), the contents of which are herein incorporated by reference in their entireties. Compounds which bind to and inhibit calmodulin activity may also inhibit $Ca^{2+}$/calmodulin dependent activation of neukinase. By way of example and not limitation, calmodulin activity in the presence and absence of potential modulators of neukinase activity may be measured using a calcium dependent phosphodiesterase assay. Calmodulin activity is measured by its ability to stimulate phosphodiesterase activity as determined by a two-step assay procedure illustrated by reactions (1) and (2) below.

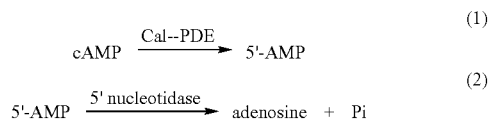

During the first step of the assay, cyclic adenosine 3'5'-monophosphate (cAMP) is incubated with calcium-activated phosphodiesterase (Cal-PDE), which hydrolyses the 3'bond producing adenosine 5'-monophosphate (5'-AMP). During the second step, 5'-AMP is quantitatively converted into adenosine and inorganic phosphate (Pi) through the action of a 5-nucleotidase. The reaction is followed by the measurement of the Pi formed by reading the absorbance at 660 nm after reacting with ammonium molybdate. The amount of Pi formed is directly related to the phosphodiesterase activity which depends on the level of activation by calmodulin.

In various embodiments, the neukinase-modulating compound is a protein, for example, an antibody; a nucleic acid; or a small molecule. As used herein, the term "small molecule" includes, but is not limited to, organic or inorganic compounds (i.e., including heteroorganic and organometallic compounds) having a molecular weight less than 10,000 grams per mole, organic or inorganic compounds having a molecular weight less than 5,000 grams per mole, organic or inorganic compounds having a molecular weight less than 1,000 grams per mole, organic or inorganic compounds having a molecular weight less than 500 grams per mole, organic or inorganic compounds having a molecular weight less than 100 grams per mole, and salts, esters, and other pharmaceutically acceptable forms of such compounds. Salts, esters, and other pharmaceutically acceptable forms of such compounds are also encompassed.

By way of example, diversity libraries, such as random or combinatorial peptide or nonpeptide libraries can be screened for molecules that specifically bind to neukinase. Many libraries are known in the art that can be used, e.g., chemically synthesized libraries, recombinant (e.g., phage display libraries), and in vitro translation-based libraries.

Examples of chemically synthesized libraries are described in Fodor et al., *Science* 251:767-773 (1991); Houghten et al., *Nature* 354:84-86 (1991); Lam et al., *Nature* 354:82-84 (1991); Medynski, *Bio/Technology* 12:709-710 (1994); Gallop et al., *J Medicinal Chemistry* 37(9):1233-1251 (1994); Ohlmeyer et al., *Proc. Natl. Acad. Sci. U.S.A.* 90:10922-10926 (1993); Erb et al., *Proc. Natl. Acad. Sci. U.S.A.* 91:11422-11426 (1994); Houghten et al., *Biotechniques* 13:412 (1992); Jayawickreme et al., *Proc. Natl. Acad. Sci. U.S.A.* 91:1614-1618 (1994); Salmon et al., *Proc. Natl. Acad. Sci. U.S.A.* 90:11708-11712 (1993); PCT Publication No. WO 93/20242; and Brenner and Lerner, *Proc. Natl. Acad. Sci. U.S.A.* 89:5381-5383 (1992).

Examples of phage display libraries are described in Scott and Smith, *Science* 249:386-390 (1990); Devlin et al., Science, 249:404-406 (1990); Christian, R. B., et al., *J. Mol. Biol.* 227:711-718 (1992)); Lenstra, *J. Immunol. Meth.* 152: 149-157 (1992); Kay et al., *Gene* 128:59-65 (1993); and PCT Publication No. WO 94/18318, published Aug. 18, 1994. In vitro translation-based libraries include but are not limited to those described in PCT Publication No. WO 91/05058, published Apr. 18, 1991; and Mattheakis et al., *Proc. Natl. Acad. Sci. U.S.A.* 91:9022-9026 (1994).

By way of examples of non-peptide libraries, a benzodiazepine library (see e.g., Bunin et al., *Proc. Natl. Acad. Sci. U.S.A.* 91:4708-4712 (1994)) can be adapted for use. Peptoid libraries (Simon et al., *Proc. Natl. Acad. Sci. U.S.A.* 89:9367-9371 (1992)) can also be used. Another example of a library that can be used, in which the amide functionalities in peptides have been permethylated to generate a chemically transformed combinatorial library, is described by Ostresh et al., *Proc. Natl. Acad. Sci. U.S.A.* 91:11138-11142 (1994).

Screening the libraries can be accomplished by any of a variety of commonly known methods. See, e.g., the following references, which disclose screening of peptide libraries: Parmley and Smith, *Adv. Exp. Med. Biol.* 251:215-218 (1989); Scott and Smith, *Science* 249:386-390 (1990); Fowlkes et al., *Bio/Techniques* 13:422-427 (1992); Oldenburg et al., *Proc. Natl. Acad. Sci. U.S.A.* 89:5393-5397 (1992); Yu et al., *Cell* 76:933-945 (1994); Staudt et al., *Science* 241:577-580 (1988); Bock et al., *Nature* 355:564-566 (1992); Tuerk et al., *Proc. Natl. Acad. Sci. U.S.A.* 89:6988-6992 (1992); Ellington et al., *Nature* 355:850-852 (1992); U.S. Pat. No. 5,096,815, U.S. Pat. No. 5,223,409, and U.S. Pat. No. 5,198,346; Rebar and Pabo, *Science* 263:671-673 (1993); and PCT Publication No. WO 94/18318, published Aug. 8, 1994.

In a specific embodiment, screening can be carried out by contacting the library members with neukinase polypeptide (or nucleic acid) immobilized on a solid phase and harvesting those library members that bind to the protein (or nucleic acid). Examples of such screening methods, termed "panning" techniques are described by way of example in Parmley and Smith, *Gene* 73:305-318 (1988); Fowlkes et al., *Bio/Techniques* 13:422-427 (1992); PCT Publication No. WO 94/18318; and in references cited herein above.

In another embodiment, the two-hybrid system for selecting interacting proteins in yeast (Fields and Song, *Nature* 340:245-246 (1989); Chien et al., *Proc. Natl. Acad. Sci. U.S.A.* 88:9578-9582 (1991)) can be used to identify molecules that specifically bind to neukinase protein or an analog thereof.

In another embodiment, screening can be carried out by creating a peptide library in a prokaryotic or eukaryotic cell, such that the library proteins are expressed on the cells' surface, followed by contacting the cell surface with neukinase and determining whether binding has taken place. Alternatively, the cells are transformed with a nucleic acid encoding neukinase, such that neukinase is expressed on the cells' surface. The cells are then contacted with a potential agonist or antagonist, and binding, or lack thereof, is determined. In a specific embodiment of the foregoing, the potential agonist or antagonist is expressed in the same or a different cell such that the potential agonist or antagonist is expressed on the cells' surface.

As would clearly be understood by a person of ordinary skill in the art, any and/or all of the embodiments disclosed herein for identifying an agent, drug, or compound that can modulate the activity of neukinase, including such procedures that incorporate rational drug design, as disclosed herein, can be combined to form additional drug screens and assays, all of which are contemplated by the present invention.

5.7 Diagnostic Methods

The present invention also pertains to the field of predictive medicine in which diagnostic and prognostic assays are used for prognostic (predictive) purposes to treat an individual prophylactically. Accordingly, one aspect of the invention relates to diagnostic assays for determining neukinase nucleic acid expression as well as neukinase activity in the context of a biological sample (e.g., blood, serum, cells, tissue) to determine whether an individual is afflicted with a disease or disorder, or is at risk of developing a disorder. Such a disease or disorder may be associated with aberrant neukinase expression or activity, and can include, but is not limited to, cardiac dysfunction. In particular embodiments, the cardiac dysfunction is hypertrophic cardiomyopathy. In other embodiments, the cardiac dysfunction is heart failure. The invention also provides for prognostic assays for determining whether an individual is at risk of developing a disorder associated with neukinase nucleic acid expression or activity. For example, mutations in neukinase can be assayed in a biological sample. Such assays can be used for prognostic or predictive purpose to prophylactically treat an individual prior to the onset of a disorder characterized by or associated with aberrant neukinase nucleic acid expression or biological activity.

5.7.1 Diagnostic Assays

An exemplary method for detecting the presence or absence of neukinase in a biological sample involves obtaining a biological sample from a subject and contacting the biological sample with a compound or an agent capable of detecting neukinase nucleic acid (e.g., mRNA, genomic DNA) such that the presence of neukinase is confirmed in the sample. An agent for detecting neukinase mRNA or genomic DNA is a labeled nucleic acid probe that can hybridize to neukinase mRNA or genomic DNA. The nucleic acid probe can be, for example, a full-length neukinase nucleic acid, such as the nucleic acid of SEQ ID NOS:3 or 4, or a portion thereof. In some embodiments, the nucleic acid probe is an oligonucleotide of at least 15, 30, 50, 100, 250 or 500 nucleotides in length and is sufficient to specifically hybridize under stringent conditions to neukinase mRNA or genomic DNA.

An agent for detecting neukinase polypeptide can be an antibody capable of binding to neukinase, preferably an antibody with a detectable label. Antibodies can be polyclonal or monoclonal. An intact antibody or an antibody fragment, e.g., a Fab fragment, can be used. A labeled probe or antibody may be coupled (i.e., physically linked) to a detectable substance, or an indirect detection method may be employed wherein the probe or antibody is detected via reactivity with a directly labeled secondary reagent. Examples of indirect labeling include detection of a primary antibody using a fluorescently labeled secondary antibody, or end-labeling of a DNA probe with biotin such that it can be detected with fluorescently-labeled streptavidin.

The detection method of the invention can be used to detect neukinase mRNA, protein, or genomic DNA in a biological sample in vitro as well as in vivo. For example, in vitro techniques for detection of neukinase mRNA include Northern hybridizations and in situ hybridizations. In vitro techniques for detection of neukinase polypeptide include enzyme linked immunosorbent assays (ELISAs), Western blots, immunoprecipitations, and immunofluorescence. In vitro techniques for detection of neukinase genomic DNA include Southern hybridizations and fluorescence in situ hybridization (FISH). Furthermore, in vivo techniques for detecting neukinase include introducing into a subject a labeled anti-neukinase antibody. For example, the antibody can be labeled with a radioactive marker whose presence and location in a subject can be detected by standard imaging techniques.

In one embodiment, the biological sample from the subject contains protein molecules, and/or mRNA molecules, and/or genomic DNA molecules. In certain embodiments, the biological sample is blood.

In another embodiment, the methods further involve obtaining a biological sample from a subject to provide a control, contacting the sample with a compound or agent to detect neukinase mRNA or genomic DNA, and comparing the presence of neukinase mRNA or genomic DNA in the control sample with the presence of neukinase mRNA or genomic DNA in the test sample.

5.7.2 Prognostic Assays

The diagnostic methods described herein can be further utilized to identify subjects having, or who are at risk of developing, a disease or disorder associated with aberrant neukinase expression or activity. Such a disease or disorder may include, but is not limited to, cardiac dysfunction, particularly hypertrophic cardiomyopathy and heart failure. The invention provides a method for identifying a disease or disorder associated with aberrant neukinase expression or activity in which a test sample is obtained from a subject and neukinase nucleic acid (e.g., mRNA, genomic DNA) is detected. A test sample is a biological sample obtained from a subject. For example, a test sample can be a biological fluid (e.g., serum), cell sample, or tissue.

Prognostic assays can be used to determine whether a subject can be administered a modality (e.g., an agonist, antagonist, peptidomimetic, protein, peptide, nucleic acid, small molecule, food, etc.) to treat a disease or disorder associated with aberrant neukinase expression or activity. Such methods can be used to determine whether a subject can be effectively treated with an agent for a disorder. The invention provides methods for determining whether a subject can be effectively treated with an agent for a disorder associated with aberrant neukinase expression or activity in which a test sample is obtained and neukinase nucleic acid is detected (e.g., where the presence of neukinase nucleic acid is diagnostic for a subject that can be administered the agent to treat a disorder associated with aberrant neukinase expression or activity).

The methods of the invention can also be used to detect genetic lesions in a neukinase gene to determine if a subject with the genetic lesion is at risk for a disorder, including but not limited to hypertrophic cardiomyopathy or heart failure. Methods include detecting, in a sample from the subject, the presence or absence of a genetic lesion characterized by an alteration affecting the integrity of a gene encoding a neukinase polypeptide, or the mis-expression of a neukinase gene. Such genetic lesions can be detected by ascertaining: (1) a deletion of one or more nucleotides from the neukinase gene; (2) an addition of one or more nucleotides to the neukinase gene; (3) a substitution of one or more nucleotides in the neukinase gene; (4) a chromosomal rearrangement of a neukinase gene; (5) an alteration in the level of neukinase mRNA transcripts; (6) aberrant modification of a neukinase gene, such as a change in genomic DNA methylation; (7) the presence of a non-wild-type splicing pattern of a neukinase mRNA transcript, (8) a non-wild-type level of a neukinase polypeptide; (9) allelic loss of neukinase; and/or (10) inappropriate post-translational modification of a neukinase polypeptide. There are a large number of known assay techniques that can be used to detect lesions in neukinase. Any biological sample containing nucleated cells may be used.

Detection of genetic lesions of neukinase may employ any technique known in the art. In certain embodiments, lesion detection may employ a nucleic acid probe/primer in a polymerase chain reaction (PCR) reaction such as anchor PCR or rapid amplification of cDNA ends (RACE) PCR. This method may include collecting a sample from a patient, isolating nucleic acids from the sample, contacting the nucleic acids with one or more nucleic acid primers that specifically hybridize to neukinase nucleic acid under conditions such that hybridization and amplification of the neukinase sequence (if present) occurs, and detecting the presence or absence of an amplification product, or detecting the size of the amplification product and comparing the length to a control sample. It is anticipated that PCR may be desirable to use as a preliminary amplification step in conjunction with any of the techniques used for detecting mutations described herein.

Mutations in a neukinase gene from a sample can also be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes can be used to score for the presence of specific mutations by development or loss of a ribozyme cleavage site.

Furthermore, hybridizing a sample and control nucleic acids, e.g., DNA or RNA, to high-density arrays containing hundreds or thousands of oligonucleotides probes can identify genetic mutations in neukinase (see Cronin et al., *Hum. Mutat.* 7:244-255 (1996); Kozal et al., *Nat. Med.* 2:753-759 (1996)). For example, genetic mutations in neukinase can be identified in two-dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the neukinase gene and detect mutations by comparing the sequence of the sample neukinase sequence with the corresponding wild-type (control) sequence. Examples of sequencing reactions include those based on classic techniques (see Maxam and Gilbert, *Proc. Natl. Acad. Sci. USA* 74:560-564 (1977); Sanger et al., *Natl. Acad. Sci. USA* 74:5463-5367 (1977)). Any of a variety of automated sequencing procedures can be used for performing diagnostic assays of the present invention (see Naeve et al., *Biotechniques* 19:448-453 (1995)) including sequencing by mass spectrometry (Cohen et al., *Adv. Chromatogr.* 36:127-162 (1996); Griffin and Griffin, *Appl. Biochem. Biotechnol.* 38:147-159 (1993)).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (see Saiki et al., *Nature* 324:163-166 (1986); Saiki et al., *Proc. Natl. Acad. Sci. USA* 86:6230-6234 (1989)). Such allele-specific oligonucleotides are hybridized to PCR-amplified target DNA or a number of different mutations when the oligonucleotides are attached to the hybridizing membrane and hybridized with labeled target DNA.

5.8 Compositions

The invention provides methods of treatment (and prophylaxis) by administration to a subject of an effective amount of a therapeutic of the invention. In a preferred aspect, the therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject. Formulations and methods of administration that can be employed can be selected from among those described herein below.

Various delivery systems are known and can be used to administer a therapeutic of the invention, e.g., encapsulation in liposomes, microparticles, microcapsules, recombinant cells capable of expressing the therapeutic, receptor-mediated endocytosis (see, e.g., Wu and Wu, *J. Biol. Chem.* 262:4429-4432 (1987)), construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the therapeutic can be delivered in a vesicle, in particular a liposome (see Langer, *Science* 249:1527-1533 (1990); Treat et al., in *Liposomes in the Therapy of Infectious Disease and Cancer*, Lopez-Berestein and Fidler (eds.), Liss, New York, pp. 317-372, 353-365 (1989)).

In yet another embodiment, the therapeutic can be delivered in a controlled release system. In one embodiment, a pump may be used (see Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability: Drug Product Design and Performance*, Smolen and Ball (eds.), Wiley, New York (1984); Ranger and Pewas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the thymus, thus requiring only a fraction of the systemic dose (see, e.g., Goodson, in *Medical Applications of Controlled Release*, supra, vol. 2, pp. 115-138 (1984)). Other controlled release systems are discussed in the review by Langer (*Science* 249:1527-1533 (1990)).

In a specific embodiment where the therapeutic is a nucleic acid encoding a protein therapeutic (e.g., SEQ ID NO:1 or SEQ ID NO:2), the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide which is known to enter the nucleus (see e.g., Joliot et al., *Proc. Natl. Acad. Sci. U.S.A.* 88:1864-1868 (1991)), etc. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* by E.W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

5.9 Kits

The pharmaceutical compositions can be included in a kit, container, pack, or dispenser together with instructions for administration. When the invention is supplied as a kit, the different components of the composition may be packaged in separate containers and admixed immediately before use. Such packaging of the components separately may permit long-term storage without losing the active components' functions.

Kits may also include reagents in separate containers that facilitate the execution of a specific test, such as diagnostic tests or tissue typing. For example, neukinase DNA templates and suitable primers may be supplied for internal controls.

5.9.1 Containers or Vessels

The reagents included in the kits can be supplied in containers of any sort such that the life of the different components are preserved, and are not adsorbed or altered by the materials of the container. For example, sealed glass ampules may contain lyophilized luciferase or buffer that have been packaged under a neutral, non-reacting gas, such as nitrogen. Ampoules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

5.9.2 Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

5.10 Methods of Treatment

The invention provides for both prophylactic and therapeutic methods of treating a subject at risk for (or susceptible to) a disorder or having a disorder associated with aberrant neukinase expression or activity. Exemplary disorders are characterized by abnormal cardiac function, including, but not limited to, congestive heart failure, myocardial infarction, tachyarrythmia, familial cardiac hypertrophy, ischemic heart disease, idiopathic dilated cardiomyopathy, myocarditis and the like.

5.10.1 Diseases and Disorders

Diseases and disorders that are characterized by increased neukinase levels or biological activity may be treated with therapeutics that antagonize (i.e., reduce or inhibit) activity. Antagonists may be administered in a therapeutic or prophylactic manner. Therapeutics that may be used include: (1) neukinase peptides, or analogs, derivatives, fragments or homologues thereof; (2) Abs to a neukinase peptide; (3) neukinase nucleic acids; (4) administration of antisense nucleic acid and nucleic acids that are "dysfunctional" (i.e., due to a heterologous insertion within the coding sequences) that are used to eliminate endogenous function of neukinase by homologous recombination (Capecchi, *Science* 244: 1288-1292 (1989)); or (5) modulators (i.e., inhibitors, agonists and antagonists, including additional peptide mimetic of the invention or Abs specific to neukinase) that alter the interaction between neukinase and its binding partner.

Diseases and disorders that are characterized by decreased neukinase levels or biological activity may be treated with therapeutics that increase (i.e., are agonists to) activity. Therapeutics that upregulate activity may be administered therapeutically or prophylactically. Therapeutics that may be used include peptides, or analogs, derivatives, fragments or homologues thereof; or an agonist that increases bioavailability, or, in a specific embodiment, an agonist that increases neukinase activity by inhibiting the autoinhibitory domain of neukinase.

Increased or decreased levels can be readily detected by quantifying peptide and/or RNA, by obtaining a patient tissue sample (e.g., from biopsy tissue) and assaying in vitro for RNA or peptide levels, structure and/or activity of the expressed peptides (or neukinase mRNAs). Methods include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

5.10.2 Prophylactic Methods

The invention provides a method for preventing, in a subject, a disease or condition associated with an aberrant neukinase expression or activity, by administering an agent that modulates neukinase expression or at least one neukinase activity. Subjects at risk for a disease that is caused or contributed to by aberrant neukinase expression or activity can be identified by, for example, any or a combination of diagnostic or prognostic assays. Administration of a prophylactic agent can occur prior to the manifestation of symptoms characteristic of the neukinase aberrancy, such that a disease or disorder is prevented or, alternatively, delayed in its progression. In a specific embodiment of the invention, ventricular muscle cell hypertrophy is prevented or delayed by administration of said prophylactic agent. Depending on the type of neukinase aberrancy, for example, a neukinase agonist or neukinase antagonist can be used to treat the subject. The appropriate agent can be determined based on screening assays.

5.10.3 Therapeutic Methods

Another aspect of the invention pertains to methods of modulating neukinase expression or activity for therapeutic purposes. The modulatory method of the invention involves contacting a cell with an agent that modulates one or more of the activities of neukinase activity associated with the cell. An agent that modulates neukinase activity can be a nucleic acid or a protein, a naturally occurring cognate ligand of neukinase, a peptide, a neukinase peptidomimetic, an aptamer, or other small molecule. The agent may stimulate neukinase activity. Examples of such stimulatory agents include active neukinase and a neukinase nucleic acid molecule that has been introduced into the cell. Stimulation of neukinase activity is desirable in situations in which neukinase is abnormally down-regulated and/or in which increased neukinase activity is likely to have a beneficial effect.

In other embodiments, the neukinase-modulating agent inhibits neukinase activity. Examples of inhibitory agents include anti-neukinase Abs, or an inhibitory nucleic acid molecule. For example, the nucleic acid molecule may comprise an antisense oligonucleotide, an aptamer, or an inhibitory/interfering RNA (e.g., a small inhibitory/interfering RNA. Methods for screening for, identifying and making these nucleic acid modulators are known in the art.

In some embodiments, RNA interference (RNAi) (see, e.g. Chuang et al., *Proc. Natl. Acad. Sci. U.S.A.* 97:4985 (2000)) can be employed to inhibit the expression of a gene encoding neukinase. Interfering RNA (RNAi) fragments, particularly double-stranded (ds) RNAi, can be used to generate loss-of-neukinase function. Methods relating to the use of RNAi to silence genes in organisms, including mammals, *C. elegans, Drosophila*, plants, and humans are known (see, e.g., Fire et al., *Nature* 391:806-811 (1998); Fire, *Trends Genet.* 15:358-363 (1999); Sharp, *Genes Dev.* 15:485-490 (2001); Hammond, et al., *Nature Rev. Genet.* 2:1110-1119 (2001); Tuschl, *Chem. Biochem.* 2:239-245 (2001); Hamilton et al., *Science* 286:950-952 (1999); Hammond et al., *Nature* 404:293-296 (2000); Zamore et al., *Cell* 101:25-33 (2000); Bernstein et al., *Nature* 409: 363-366 (2001); Elbashir et al., *Genes Dev.* 15:188 200 (2001); Elbashir et al. *Nature* 411:494-498 (2001); International PCT application No. WO 01/29058; and International PCT application No. WO 99/32619), the contents of which are incorporated by reference. Double-stranded RNA (dsRNA)-expressing constructs are introduced into a host using a replicable vector that remains episomal or integrates into the genome. By selecting appropriate sequences, expression of dsRNA can interfere with accumulation of endogenous mRNA encoding neukinase.

Modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of a neukinase or nucleic acid molecule. In one embodiment, the method involves administering an agent (e.g., an agent identified by a screening assay), or combination of agents that modulates (e.g., up-regulates or down-regulates) neukinase expression or activity. In another embodiment, the method involves administering a neukinase or nucleic acid molecule as therapy to compensate for reduced or aberrant neukinase expression or activity.

5.10.4 Determination of the Biological Effect of the Therapeutic

Suitable in vitro or in vivo assays can be performed to determine the effect of a specific therapeutic and whether its administration is indicated for treatment of the affected tissue.

In various specific embodiments, in vitro assays may be performed with representative cells of the type(s) involved in the patient's disorder, to determine if a given therapeutic exerts the desired effect upon the cell type(s). Modalities for use in therapy may be tested in suitable animal model systems including, but not limited to rats, mice, chicken, cows, monkeys, rabbits, and the like, prior to testing in human subjects.

Similarly, for in vivo testing, any of the animal model systems known in the art may be used prior to administration to human subjects. In one embodiment, a candidate therapeutic may be tested for efficacy in an in vivo model for cardiac hypertrophy. The in vivo determination of hypertrophy includes measurement of cardiovascular parameters such as blood pressure, heart rate, systemic vascular resistance, contractility, force of heart beat, concentric or dilated hypertrophy, left ventricular systolic pressure, left ventricular mean pressure, left ventricular end-diastolic pressure, cardiac output, stroke index, histological parameters, and ventricular size and wall thickness. Animal models available for determination of development and suppression of ventricular muscle cell hypertrophy in vivo include the pressure-overload mouse model, RV murine dysfunctional model, transgenic mouse model, and post-myocardial infarction rat model. Medical methods for assessing the presence, development, and suppression of ventricular muscle cell hypertrophy in human patients are known, and include, for example, measurements of diastolic and systolic parameters, estimates of ventricular mass, and pulmonary vein flows.

5.10.5 Prophylactic and Therapeutic Uses of the Compositions of the Invention

Neukinase nucleic acids and proteins are useful in potential prophylactic and therapeutic applications implicated in a variety of disorders including, but not limited to, congestive heart failure, myocardial infarction, tachyarrythmia, familial cardiac hypertrophy, ischemic heart disease, idiopathic dilated cardiomyopathy, myocarditis and the like.

As an example, a cDNA encoding neukinase may be useful in gene therapy, and the protein may be useful when administered to a subject in need thereof. By way of non-limiting example, the compositions of the invention will have efficacy for treatment of patients suffering from heart failure.

Neukinase nucleic acids, or fragments thereof, may also be useful in diagnostic applications, wherein the presence or amount of the nucleic acid or the protein is to be assessed. A further use could be as an anti-bacterial molecule (i.e., some peptides have been found to possess anti-bacterial properties). These materials are further useful in the generation of Abs that immunospecifically bind to the novel substances of the invention for use in therapeutic or diagnostic methods.

6. EXAMPLES

The invention is illustrated by the following examples which are not intended to be limiting in any way.

6.1 Example 1

Upregulation of Neukinase Gene Expression Following Application of Neuregulin in Myocardial Infarcted Rat Left Ventricle In order to identify genes which may be regulated by neuregulin (NRG), gene expression was examined in both normal and myocaridal infarcted rat left ventricle following extended infusion of NRG by osmotic pump.

To charge an osmotic pump with NRG, 1 ml of sterile water and 1 ml of sterile 0.9% saline was injected into a vial of NRG (993.1 U, 62.5 μg) in the hood successively. The NRG solution was drawn into a sterile syringe. A blunt-tipped needle was exchanged for the syringe and the bubble in the syringe was removed. The pump was held upright and the needle was inserted through the small opening at the top of the upright pump until it could go no further. The plunger was pushed slowly to add NRG solution into the pump until the solution began to overflow the pump. The needle was removed and the pump was wiped clean. The transparent cap of the flow moderator was taken off to expose a short stainless steel tube. The steel tube was then inserted into one end of a 5 cm PE60 tube. The syringe needle was inserted into another end of the PE60 tube. The plunger of the syringe was pushed to add NRG solution to the flow moderator until it was full. The long tube of the flow moderator was then inserted into the pump until its white flange attached to the pump. The needle was drawn out of the flow moderator before soaking the pump in sterile 0.9% saline at 37° C. overnight.

To install the osmotic pump, Wistar male rats (Shanghai Animal Center of Chinese Academy of Science), each of which weighed 200±20 g, were anesthetized by intraperitoneally injecting 100 mg/kg (drug/body weight) of ketamine. The area between neck and shoulder of the rats was depilated and sanitized. The body was covered with a piece of sterile wet cloth. An incision was then carefully made in the skin between the scapulae to locate and separate the external jugular vein. The distal end of the vein from the heart was ligated. A small hole was made by eye scissors on the wall of the external jugular vein and enlarged by microforceps. The PE60 tube connected to the osmotic pump was inserted 2 cm into the vein through the hole. The proximal end of the vein from the heart was then bound with PE60 tube to fix the tube. The distal end of the vein surrounding the PE60 tube was tied tight to further fix the tube. Using a hemostat, a tunnel was formed by blunt separation of the skin from the incision to scapula. A pocket was finally made on the back of the rat in the midscapular region by spreading the skin further. The pump was slid through the tunnel into the pocket with the flow moderator pointing away from the incision. The skin incision was then closed with a suture. The rats were put back into the animal room after revival and were fed as usual.

After MI rats were treated with NRG through the osmotic pump for 7 days, the rats were sacrificed and their left ventricles were taken and sent to Affymetrix, Inc. for gene expression analysis. The rat left ventricle was then homogenized and total mRNA was extracted from the homogenate. The mRNA sample was then studied by Affymetrix Rat expression array 230 2.0 and the mRNA level of genes were examined using a microarray. The calculated levels of mRNA corresponding to proteins related to myosin light chain kinase are listed in Table 1. Each data point represents the average expression levels from 3 rats.

TABLE 1

Relative Levels Of mRNAs Encoding Proteins Related To Myosin Light Chain Kinase From Rat Left Ventricle Treated with NRG

| Probe set ID | Normal rats with vehicle | MI rats with vehicle | MI rats with NRG | Gene |
| --- | --- | --- | --- | --- |
| 1371541 | 0.921 ± 0.085 | 0.951 ± 0.125 | 1.147 ± 0.165 | Myosin, light polypeptide kinase (predicted) |
| 1376789 | 0.997 ± 0.066 | 0.679 ± 0.098 | 1.696 ± 0.189 | Similar to Myosin light chain kinase 2, skeletal/cardiac muscle (predicted) |
| 1382239 | 0.886 ± 0.218 | 0.591 ± 0.246 | 1.721 ± 0.339 | Similar to myosin light chain kinase 2, skeletal/cardiac muscle (predicted) |
| 1384818 | 0.908 ± 0.296 | 0.598 ± 0.227 | 0.335 ± 0.162 | Myosin, light polypeptide kinase (predicted) |
| 1386200 | 0.969 ± 0.274 | 0.717 ± 0.104 | 0.946 ± 0.098 | Similar to Myosin light chain kinase 2, skeletal/cardiac muscle (predicted) |
| 1398820 | 0.942 ± 0.185 | 1.115 ± 0.101 | 0.592 ± 0.195 | myosin light chain kinase 2, skeletal muscle |
| 1398821 | 0.700 ± 0.254 | 1.287 ± 0.375 | 0.738 ± 0.217 | myosin light chain kinase 2, skeletal muscle |

For mRNA sequences hybridizing to probe sets 1376789 and 1382239, expression was increased at least 2-fold in NRG-treated MI rat left ventricle compared to control (vehicle)-treated samples. These results demonstrate that NRG significantly enhances the level of mRNAs that bind with probe set 1376789 and/or 1382239 in MI rat left ventricle. Accordingly, mRNAs that bind to probe set 1376789 or 1382239 likely encode proteins which are downstream target(s) of neuregulin.

6.2 Example 2

Cloning Of Neukinase cDNA From Rat Left Ventricle RNA

Total RNA was extracted from normal rat left ventricle. RNA, primer (GACTCGAGTCGACATC-GATTTTTTTTTTTTTTTTT (SEQ ID NO:5)) and AMV reverse transcriptase (Promega) were added to the Promega Reverse Transcription System (cat. #A3500), and reverse transcription was performed according to the manufacturer's protocol. After the reaction, an aliquot of the reaction mixture, reverse primer (GACTCGAGTCGACATC-GATTTTTTTTTTTTTTTTT (SEQ ID NO:5)) and forward primer (ATGTCAGGAGTTTCAGAGGA (SEQ ID NO:6)) (based on predicted similarity to myosin light chain kinase 2) were added to a PCR master mix (Sinobio) to amplify target cDNA by PCR. Following PCR, the resulting sample was purified by electrophoresis and ligated to pUCm-T plasmid (Promega). The plasmid was then sequenced with the two primers mentioned above (SEQ ID NOS: 5 and 6). The cDNA sequence is listed as SEQ ID NO:1, and the corresponding protein amino acid sequence is listed as SEQ ID NO:2. This protein was named neukinase, and its cDNA sequence was further confirmed by alignment with the sequences for probe set 1382239 (SEQ ID NO:9) and probe set 1376789 (SEQ ID NO:10) (see Example 1 above). Alignment of these three sequences to the rat genome revealed that 325 bp of the 5' end of SEQ ID NO: 9 overlapped with the 3' end of the neukinase gene, and 77 bp of the 5' end of SEQ ID NO:10 overlapped with the 3' of SEQ ID NO:9.

6.3 Example 3

Specific Expression of the Neukinase Gene in Rat Heart

Using neukinase cDNA as template, a subsequence of neukinase (SEQ ID NO:8) was synthesized by PCR using a forward primer (ATGTCAGGAGTTTCAGAGGA (SEQ ID NO:6)) and a reverse primer (CTTGAATTCTCACAGT-GACGTATCGATGAT (SEQ ID NO:7)). This fragment (SEQ ID NO:8) was then purified and used as a template to synthesize a radiolabeled neukinase cDNA probe. The neukinase cDNA fragment and [($\alpha$-$^{32}$P]dCTP were added to Promega's Prime-a Gene® labeling system (containing DNA polymerase I large fragment and random hexadeoxyribonucleotides) to synthesize labeled probes. Reaction products were loaded onto Sephacryl® S-400 spin columns (Promega), and columns were spun to harvest probes longer than 270 bp. Probes were then used for Northern Blot analysis of Clontech's Rat MTN™ blot, which includes poly A$^+$ RNA extracted from various rat organs (heart, brain, spleen, lung, liver, skeletal muscle, kidney and testis). FIG. 1 shows that neukinase specific probe hybridized only with an mRNA of approximately 4.4 kb from heart tissue, suggesting that the neukinase gene is a cardiac specific gene. The blot was also hybridized with β-actin specific probe (Clontech) as a loading control.

6.4 Example 4

Cloning of Human Neukinase cDNA from Human Left Ventricle RNA

Total RNA was extracted from human left ventricle. RNA, Oligo dT primer ((TTTTTTTTTTTTTTT)) and AMV reverse transcriptase (Promega) were added to the Promega Reverse Transcription System for reverse transcription. After the reaction, an aliquot of the reaction mixture, forward primer (GACACCACCGCCTGAGTGAGAAC (SEQ ID NO:11)) and reverse primer (CCATTGGAGCAGCA-GAGTTGAAGA (SEQ ID NO:12)) was added to a PCR master mix (Sinobio), and PCR was performed to amplify target cDNA. After the reaction, the resulting mixtures were purified by electrophoresis and ligated to pUCm-T plasmid (Promega) and sequenced. The human neukinase cDNA sequence is listed as SEQ ID NO:4. Putative alternative translation start sites were identified at positions 139 and 211 of SEQ ID NO:4, translation from which results in polypeptides of 795 amino acids (SEQ ID NO:2) and 819 amino acids (SEQ ID NO:25), respectively.

6.5 Example 5

Human Neukinase Antibody Production

Rabbit polyclonal antibodies against a human neukinase-GST fusion protein were generated. Briefly, human neukinase cDNA, forward primer (CGCGGATCCATGGACA-CAAAGCTGAACATG (SEQ ID NO:13)) and reverse primer (CCTTAAGTCACGTGGCCCCCACCAAAGC-GAT (SEQ ID NO:14)) were added to a PCR master mix (Sinobio), and PCR was performed. After the PCR, the resulting mixtures were purified by electrophoresis. Both the purified DNA and pGEX-2T plasmid (GE healthcare) were digested by BamHI and EcoRI respectively before ligation. The cDNA sequence of human neukinase fragment is listed as SEQ ID NO:15, and the amino acid sequence of the fragment is shown as SEQ ID NO:16.

The ligated construct containing human neukinase fragment cDNA was transformed into BL21 cells before IPTG was added to the culture to induce high expression of neukinase fragment. The cells were collected by centrifugation of the culture before sonication. The sonicated cell suspension was further centrifuged to pellet inclusion bodies. After removal of the supernatant, 8M urea was added to dissolve the inclusion bodies. The neukinase fragment solution was then dialysed to remove urea and to simultaneously refold the fragment. The fragment was then purified by GST affinity column and hypodermically injected to Rabbit to produce antibody. After 2 weeks, rabbit serum was drawn for purification of antibody.

6.6 Example 6

Specific Expression of Neukinase in Human Heart Tissue

Tissues from human gut, liver, heart, skeletal muscle, lung, kidney, uterus, spleen and thyroid were homogenized separately and lysed with lysis buffer (50 mM Tris, pH 7.4, 150 mM NaCl, 1% Triton X-100, 5 mM EDTA, 50 mM NaF, 2 mM Sodium Vanadate, 2 mM PMSF, cocktail protease inhibitor (Roche, 1 piece for 25 ml)). Protein samples from lysed tissues were subjected to SDS-PAGE, then transferred to a PVDF membrane for Western blot. The expression of neukinase protein in different human tissues was detected by the antibody produced in example 5. The membrane was probed with a GAPDH-specific antibody as a loading control. As shown in FIG. 2, neukinase was only expressed in human heart. This result complements the mRNA expression of neukinase in rat heart tissue, as presented in example 3, and further demonstrates that expression of neukinase is cardiac specific.

6.7 Example 7

Human Neukinase Activity is Calcium and Calmodulin Dependent

Expression and Purification of Human Regulatory Myosin Light Chain (RLC)

Total RNA was extracted from human left ventricle tissue. RNA, forward primer (GGGAATTCCATATGGCAC-CTAAGAAAGCAAAGAA (SEQ ID NO:17)), reverse primer (CCGCTCGAGGTCCTTCTCTTCTCCGTGGGTG (SEQ ID NO:18)) and AMV reverse transcriptase were added to the Promega Reverse Transcription System for reverse transcription. After the reaction, double stranded cDNA was ligated to pet22b plasmid. The ligated construct was then transformed into BL21 cells before IPTG was added to induce high expression of his-tagged RLC. Cells were pelleted by centrifugation before sonication to release inclusion bodies. Inclusion bodies were collected by further centrifugation before being dissolved by 8M urea. Denatured his-tagged RLC was purified by nickel column and refolded by dialysis to remove urea. The amino acid sequence of RLC corresponds with SEQ ID NO:19.

Recombinant Expression and Purification of Neukinase

Neukinase cDNA, forward primer (CATCATCTGGTTC-CGCGTGGATCTATGTCAGGAACCTCCAAGGAGAGT (SEQ ID NO: 20)), reverse primer (CGGAATTCCCATTG-GAGCAGCAGAGTTGAAG (SEQ ID NO:21)) and Pfu Turbo® DNA polymerase (Stratagene) were added to the PCR reaction system for PCR. Following several rounds of amplification, an aliquot of the reaction mixture, new forward primer (CGGGATCCATGCATCATCATCATCAT-CATCTGGTTCCGCGT (SEQ ID NO:22)), reverse primer (CGGAATTCCCATTGGAGCAGCAGAGTTGAAGA (SEQ ID NO:21) and PfuTurbo® DNA polymerase (Stratagene) were added to PCR reaction system for additional rounds of PCR. DNA in the reaction mixture was separated by electrophoresis, and target DNA encoding neukinase was purified and ligated to pcDNA3 plasmid. Ligation reaction products were transformed into DH5α cells for amplification and sequencing. Clones containing the correct construct were amplified in scale-up cultures, and plasmid DNA containing neukinase cDNA was extracted using the Qiagen Plasmid Maxi Kit. Purified pcDNA3/neukinase plasmid was then transfected into COS7 cells using Lipofectamine™ 2000 (Invitrogen). After an initial change of media several hours following transfection, cells were incubated for 48 hours at 37° C. Cells were then lysed and harvested using lysis buffer (50 mM Tris, pH 7.4, 150 mM NaCl, 1% Triton X-100, 5 mM EDTA, 50 mM NaF, 2 mM Sodium Vanadate, 2 mM PMSF, cocktail protease inhibitor (Roche, 1 tablet for 25 ml lysis buffer)). The cell suspension was centrifuged at 12000 g for 20 minutes, and resuspended pellets were filtered through a 0.45 µm membrane (Millipore). The sample was then mixed with His-tag antibody (Beyotime) and 50% Protein A Sepharose 4 Fast Flow in lysis buffer and incubated on ice for 3 hours with gentle shaking. The mixture was centrifugated at 12000 g for 20 seconds before the supernatant was removed. The pellet was then washed three times with lysis buffer. Following the last wash, the pellet was resuspended in 1 ml of reaction buffer (20 mM Tris, pH 7.5, 60 mM KCl), mixed and incubated on ice for five minutes. The mixture was then centrifuged, the supernatant removed, and another 300 µl reaction buffer was added.

Calcium and Calmodulin-Dependent Phosphorylation of RLC by Neukinase

In-vitro phosphorylation assays were performed utilizing purified neukinase, RLC, and Calmodulin (Calbiochem) to determine whether neukinase phosphorylation of RLC is both calcium and calmodulin dependent. The activity of neukinase was assessed in vitro, both in the presence and absence of Ca2+ and calmodulin, by monitoring the amount of RLC phosphorylation, as determined by Western blotting for phosphorylated RLC (RLC-P). Three experiments were performed simultaneously. In experiment 1, the reaction components included neukinase, ATP, RLC, Ca+, CaM. In experiment 2, the reaction components included neukinase, ATP, RLC, CaM, but not calcium, and EGTA was added to chelate calcium in the reaction buffer. In experiment 3, the reaction components included neukinase, ATP, RLC, and $Ca^{2+}$, but not calmodulin. The concentration of reactants, when included in the reaction, were as follows: 2 mM ATP, 2.5 µM RLC, 0.3 µM $Ca^{2+}$, 1 µM CaM, with or without 2 mM EGTA. Phosphorylation reactions were carried out at room temperature for 2 hours with gentle shaking. A 20 µl aliquot of each reaction was removed, subjected to polyacrylamide gel electrophoresis, and transferred to a PVDF membrane for Western blot analysis. RLC-P antibody (Cell Signaling) was used to detect RLC-P; the results are presented in FIG. 3.

RLC is highly phosphorylated when neukinase is combined with RLC in the presence of both $Ca^{2+}$ and calmodulin (lane 1). In contrast, RLC phosphorylation is barely detectable in the absence of $Ca^{2+}$ combined with the addition of EGTA to the reaction solution (lane 2). Similarly, RLC phosphorylation is undetectable in the absence of calmodulin (lane 3). Taken together, these results indicate that neukinase phosphorylation of RLC is highly dependent on the presence of $Ca^{2+}$ and calmodulin. Thus, it is believed that the neukinase phosphorylation of RLC occurs in the following manner:

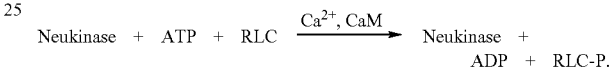

$$\text{Neukinase} + \text{ATP} + \text{RLC} \xrightarrow{Ca^{2+},\ CaM} \text{Neukinase} + \text{ADP} + \text{RLC-P}.$$

In the formula, CaM stands for Calmodulin, RLC stands for regulatory myosin light chain, and RLC-P stands for phosphorylated RLC.

6.8 Example 8

The Activity of Human Neukinase Expressed in Insect Cells

Preparation of Bacmid Containing Human Neukinase cDNA pcDNA3/neukinase plasmid DNA from example 7 was digested with BamHI and EcoRI to excise the neukinase cDNA fragment. Digestion products were separated by electrophoresis, and the human neukinase cDNA fragment was gel purified and subsequently ligated to pFastBac plasmid DNA digested with EcoRI BamHI. DH5α competent cells were transformed with the ligation products, plated, and incubated overnight. Mini-prep DNA isolated from several overnight colonies were sent to Invitrogen for sequencing to identify neukinase positive clones. Colonies harboring pFastBac/neukinase plasmids containing the correct neukinase cDNA sequence were amplified further, and plasmid DNA was purified using a Plasmid Maxi Kit (Qiagen). pFastBac/neukinase plasmid DNA was then transformed into DH10Bac cells, and the cells were inoculated onto an agarose plate containing 50 µg/ml kanamycin, 7 µg/ml gentamicin, 10 µg/ml tetracycline, 200 µg/ml X-gal and 40 µg/ml IPTG and incubated at 37° C. for 48 hours. A white colony was picked out and inoculated again onto a new agarose plate containing 50 µg/ml kanamycin, 7 µg/ml gentamicin, 10 µg/ml tetracycline, 200 µg/ml X-gal and 40 µg/ml IPTG and incubated at 37° C. overnight. A white colony was then inoculated into liquid media containing 50 µg/ml kanamycin, 7 µg/ml gentamicin and 10 µg/ml tetracycline and gently shaken overnight at 37° C. 6 ml of the liquid culture was taken and centrifuged at 14000 g for 1 min. The supernatant was removed, and 1.2 ml of solution 1 (15 mM Tris-HCl, pH8.0, 10 mM EDTA, 100 µg/ml RNase A) was added and mixed gently to resuspend the cells. 1.2 ml of solution 2 (0.2N NaOH, 1% SDS) was then added and mixed gently at room temperature for 5 minutes.

1.2 ml 3M potassium acetate, pH 5.5 was added slowly while shaking, and the mixture was centrifugated at 14000 g for 10 minutes. The supernatant was transferred to a tube containing 3.2 ml isopropanol. The tube was inverted several times and left on ice for 6 minutes before centrifugation at 14000 g for 15 min. The supernatant was removed carefully without disturbing the pellet. 2 ml of 70% ethanol was added to the pellet before the tube was turned upside down several times and centrifuged at 14000 g for 5 minutes. The tube was left open at room temperature for 5-10 min and the pellet allowed to following removal of residual supernatant. 40 µl TE buffer, pH8.0 was added to dissolve the purified Bacmid DNA.

Purified Bacmid DNA, forward primer (GTTTTCCCAGTCACGAC (SEQ ID NO:23), also M13+) and reverse primer (CGGAATTCCCATTGGAGCAGCAGAGTTGAAGA (SEQ ID NO: 24)) were added to a PCR master mix (Sinobio) for PCR. The reaction mixture was then electrophoresed to detect the positive clone.

Expression and Purification of Human Neukinase 5.4×10⁶ sf9 insect cells were seeded on a 10 cm plate in Grace's insect medium (Invitrogen) and left at room temperature for 1 hour. During this time, 24 µg of Bacmid containing human neukinase cDNA (Bacmid/neukinase) was added to 1.5 ml Grace's medium (without antibiotics and FBS) and mixed. 60 µl Lipofectamine™ 2000 (Invitrogen) was mixed with 1.5 ml Grace's medium (without antibiotics and FBS) and incubated at room temperature for 5 min. The Bacmid/neukinase-containing solution was mixed with the diluted Lipofectamine™ 2000 and incubated at room temperature for 20 min. 2 ml Grace's medium (without antibiotics and FBS) was added, and the entire solution was added to sf9 cells following replacement of the medium. After 5 hours of incubation, the medium was removed at 27° C. and replaced with 10 ml Grace's medium (with 100 U streptomycin, 100 U ampicillin and 10% FBS). Medium was collected after 72 hours incubation at 27° C. The medium was centrifuged for 5 minutes at 500 g, and the supernatant containing virus was stored at 4° C. in the dark for short-time storage and at −80° C. for long-term storage.

Virus-containing solution was added to Sf9 cells that were allowed to attach to tissue culture plastic for 1 hour. After the cells were incubated in virus-containing medium at 27° C. for 72 hours, the medium was collected, and a small amount was added to a 100 ml Sf9 cell suspension in a bottle (2×10⁶ cells/ml). The suspension was incubated at 27° C. for 84 hours with shaking (shaking speed: 130 rpm). After incubation, the cell suspension was collected and centrifuged at 1000 rpm for 10 minutes, and the supernatant was removed. Lysis buffer (50 mM Tris, pH 7.4, 150 mM NaCl, 1% Triton X-100, 5 mM EDTA, 50 mM NaF, 2 mM Sodium Vanadate, 2 mM PMSF, cocktail protease inhibitor (Roche, 1 piece for 25 ml)) was then added to the cell pellet and the cell suspension was sonicated before centrifugation at 12000 rpm for 20 minutes. The supernatant was then filtered before loading onto a Nickel column (Ni sepharose high performance, GE) to purify human neukinase. The protein solution was loaded onto a gel filtration column (HiTrap Desalting column, GE) to further purify the protein, and the protein was washed from the column with buffer containing 50 mM Tris-HCl, pH 7.5, 150 mM NaCl, 0.5 mM EDTA, 0.02% Triton X-100, 2 mM DTT, 20% glycerol. The human neukinase solution was aliquoted and stored at −80° C.

Assessment of Human Neukinase Activity

The following provides an exemplary method for determining neukinase activity in-vitro. Phosphorylation of RLC by neukinase involves the following reactions and reaction products:

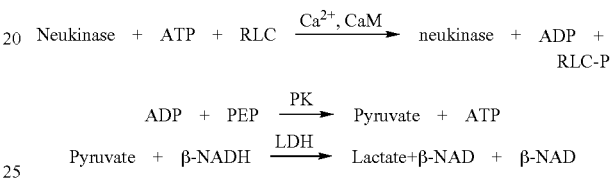

$$\text{Neukinase} + \text{ATP} + \text{RLC} \xrightarrow{\text{Ca}^{2+}, \text{CaM}} \text{neukinase} + \text{ADP} + \text{RLC-P}$$

$$\text{ADP} + \text{PEP} \xrightarrow{\text{PK}} \text{Pyruvate} + \text{ATP}$$

$$\text{Pyruvate} + \beta\text{-NADH} \xrightarrow{\text{LDH}} \text{Lactate} + \beta\text{-NAD} + \beta\text{-NAD}$$

In the formula, PEP stands for phosphoenolpyruvate; PK stands for pyruvate kinase; β-NADH stands for β-Nicotinamide Adenine Dinucleotide (reduced form); LDH stands for Lactic Dehydrogenase; and β-NAD stands for β-Nicotinamide Adenine Dinucleotide (oxidized form).

Thus, neukinase activity can be determined by measuring the rate of decrease of NADH absorbance at 340 nm, which is proportional to the rate of steady-state ATP hydrolysis by neukinase. This assay can also be used to detect agents which can enhance or inhibit the activity of neukinase. In the assay, an 800 µl reaction comprises: 20 mM Tris, pH 7.5, 60 mM KCl, 1 mM DTT, 3.75 mM MgCl₂, 1 mM ATP, 0.3 µM CaCl₂, 1.5 mM PEP, 20 U/ml PK, 20 U/ml LDH, 90 µM RLC, 250 µM β-NADH, 1 µM CaM and 100 nM neukinase, ΔOD/min/nmol nukinase=0.0152/min/nmol neukinase.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying genetic predisposition of a subject to cardiac dysfunction associated with aberrant expression of neukinase, said method comprising:
   (a) detecting a level of expression of a polypeptide comprising SEQ ID NO:25 in a sample derived from said subject by contacting said sample with an anti-neukinase antibody comprising a detectable label, wherein said antibody is selective for a polypeptide sequence of SEQ ID NO:25 and detecting binding between said polypeptide and said antibody;
   (b) detecting a level of expression of said polypeptide in a control sample by contacting said control sample with said anti-neukinase antibody and detecting binding between said polypeptide and said antibody; and
   (c) comparing said detected level of expression of said polypeptide from said sample to said detected level of expression of said polypeptide in said control sample; wherein decreased expression of said polypeptide in said sample compared to said control sample indicates that said subject is genetically predisposed to cardiac dysfunction.

2. The method of claim 1, wherein said cardiac dysfunction is heart failure.

3. The method of claim 2, wherein said heart failure is selected from the group consisting of congestive heart failure, myocardial infarction, tachyarrhythmia, familial hypertrophic cardiomyopathy, ischemic heart disease, idiopathic dilated cardiomyopathy, and myocarditis.

4. The method of claim 3, wherein said heart failure is ischemic, congenital, rheumatic, or idiopathic.

5. The method of claim 2, wherein said heart failure is hypertrophic cardiomyopathy.

6. The method of claim 1, wherein said subject is a mammal.

7. The method of claim 6, wherein said subject is a human.

8. The method of claim 1, wherein said detecting of said polypeptide of SEQ ID NO:25 is performed in-vitro or in-vivo.

9. The method of claim 1, wherein said detection is performed using an enzyme linked immunosorbent assay (ELISA), a Western Blot, an immunoprecipitation assay, immunofluorescence, or a combination thereof.

10. The method of claim 1, wherein said antibody comprises an intact antibody or an antibody fragment.

11. The method of claim 1, wherein said detectable label comprises a radioactive marker.

12. The method of claim 1, wherein said detection comprises quantifying an amount of said expression.

13. The method of claim 1, wherein said sample is a biological fluid, a cell, or a tissue.

* * * * *